United States Patent [19]
Bosslet et al.

[11] Patent Number: 5,959,083
[45] Date of Patent: Sep. 28, 1999

[54] TETRAVALENT BISPECIFIC RECEPTORS, THE PREPARATION AND USE THEREOF

[75] Inventors: Klaus Bosslet, Marburg; Gerhard Seemann, Marburg-Elnhausen, both of Germany

[73] Assignee: Behringwerke Aktiengellschaft, Marburg, Germany

[21] Appl. No.: 08/308,494

[22] Filed: Sep. 21, 1994

Related U.S. Application Data

[63] Continuation of application No. 08/109,986, Aug. 23, 1993, abandoned, which is a continuation of application No. 07/891,739, Jun. 1, 1992, abandoned.

[30] Foreign Application Priority Data

Jun. 3, 1991 [DE] Germany .................. 41 18 120

[51] Int. Cl.$^6$ ................ C07K 16/46; A61K 31/395; C12N 15/13
[52] U.S. Cl. ............... 530/387.3; 530/389.9; 530/388.3; 530/866; 530/869; 530/389.7; 530/387.1; 435/70.21; 435/172.2; 435/253.3; 435/320.1; 435/69.7; 435/188.5; 424/130.1; 424/133.1; 424/134.1; 424/135.1; 424/143.1; 424/155.1; 424/174.1
[58] Field of Search ............. 530/387.3, 388.9, 530/388.3, 866, 861, 389.9, 387.1, 389.7; 435/70.21, 172.2, 210 A, 253.3, 320.1, 69.7, 188.5; 424/130.1, 133.1, 134.1, 135.1, 143.1, 155.1, 174.1

[56] References Cited

FOREIGN PATENT DOCUMENTS

| | | |
|---|---|---|
| 2025607 | 3/1991 | Canada . |
| 0 404 097 A2 | 12/1990 | European Pat. Off. . |
| 404097 | 12/1990 | European Pat. Off. ........ C01K 15/28 |
| 0 419 387 A1 | 3/1991 | European Pat. Off. . |
| WO 91/03493 | 3/1991 | WIPO . |

OTHER PUBLICATIONS

Waldmann [Science 252:1657–1662 (1991)].
Harris et al. [TIBTECH 11:42–44 (1993) ].
Osband et al. [Immunotherapy 11(6):193–195 (1990)].
Hird et al. [Genes and Cancer (1990) chapter 17].
Curti [Critical Reviews in Oncology/Hematology 14:29–39 (1993)].
Cunningham et al. [TIBTECH 10(4):112–113 (1992)].
Kettleborough et al. [Protein Engineering 4(7):773–783 (1991)].
Dillman et al. [Ann. Int. Med 111:592–603 (1989)].
L. Anderson et al.; "Comparison of DOTA and DTPA Analogs for Bifunctional Antibody Delivery of Indium–111 and Yttrium–90"; Journal of Nuclear Medicine, vol. 32, No. 5, May 1991, pp. 915–916.
K. Bosslet et al.; "Generation of Bispecific Monoclonal Antibodies for Two Phase Radioimmunotherapy"; British Journal of Cancer, vol. 63, No. 5, May 1991, pp. 681–686.

J. Le Doussal et al.; "Targeting of Indium 111–labeled Bivalent Hapten to Human Melanoma Medieated By Bispecific Monoclonal Antibody Conjugates: Imaging of Tumors Hosted in Nude Mice"; Cancer Research, vol. 50, No. 11, Jun. 1990, pp. 3445–3452.

H. Paulus, Preparation and Biomedical Applications of Bispecific Antibodies, Behring Inst. Mitteilungen, (1985), No. 78, pp. 118–132.

Uwe D. Staerz and Michael J. Bevan, hybrid hybridoma producing a bispecific monoclonal antibody that can focus effector T–cell activity, Proc. Natl. Acad. Sci. USA, vol. 83, pp. 1453–1457, Mar. 1986.

J. van Dijk et. al., Induction of Tumor–Cell Lysis Bi–Specific Monoclonal Antibodies Recognizing Renal–cell Carcinoma and CD3 Antigen, Int. J. Cancer: 43, (1989), pp. 344–349.

(List continued on next page.)

*Primary Examiner*—Frank C. Eisenschenk
*Attorney, Agent, or Firm*—Finnegan, Henderson, Farabow, Garrett & Dunner, L.L.P.

[57] ABSTRACT

The invention relates to bispecific tetravalent receptors of the formula I or formula II against a tumor-associated antigen and against an agent active against tumors.

9 Claims, 33 Drawing Sheets

OTHER PUBLICATIONS

Rosaria Orlandi et. al., Cloning immunoglobulin vairiable domains for expression by the polymerase chain reaction, Proc. Natl. Acad. Sci. USA, vol. 86, pp. 3833–3837, May 1989.

Frank Lee et.al., Glucocorticoids regulate expression of dihydrofolate reductase cDNA in mouse mammary tumour virus chimaeric plasmids, Nature, vol. 294, pp. 228–232, Nov. 19, 1981.

Hudziak et al.; Establishment of Mammalian Cell Lines Containing Multiple Nonsense Mutations and Functional Suppressor tRNA Genes, Cell, vol. 31, pp. 137–146, Nov. 1982.

Biochim. Biophys. Acta Protein Struct. Mol. Enzymol. (Netherlands) 1990, 1040/1 (1–11) Nolan et al.

VH

```
  Q   V   Q   L   Q   E   S   G   G   G   L   V   Q   P   G   G   S   L   R   L
CAGGTCCAACTGCAGGAGTCTGGAGGAGGCTTGGTACAGCCTGGGGGTTCTCTGAGACTC
         10        20        30        40        50        60

S   C   A   T   S   G   F   S   D   Y   Y   M   N   W   V   R   Q   P   P   G
TCCTGCGCAACTTCTGGGTTCAGTGATTACTACATGAACTGGGTCCGCCAGCCTCCAGGA
         70        80        90       100       110       120

K   A   L   E   W   L   G   F   I   S   N   K   P   N   G   H   T   T   E   Y
AAAGCACTTGAGTGGTTGGGTTTTATTTCAAACAAACCTAATGGTCACACAACAGAGTAC
        130       140       150       160       170       180

S   A   S   V   K   G   R   F   T   I   S   R   D   N   S   Q   S   I   L   Y
AGTGCATCTGTGAAGGGTCGGTTCACCATCTCCAGAGATAATTCCCAAAGCATCCTCTAT
        190       200       210       220       230       240

L   Q   M   N   T   L   R   A   E   D   S   A   T   Y   Y   C   A   R   D   K
CTTCAAATGAACACCCTGAGAGCTGAGGACAGTGCCACTTATTATTGTGCAAGAGATAAG
        250       260       270       280       290       300

G   I   R   W   Y   F   D   V   W   G   Q   G   T   T   V   T   V   S   S
GGAATACGATGGTACTTCGATGTCTGGGGCCAAGGGACCACGGTCACCGTCTCCTCA
        310       320       330       340       350
```

```
         A   I   L   S   A   S   P   G   E   K   V   T   M   T   C   R   A   S   S   S
       AGCAATCCTGTCTGCATCTCCAGGGGAGAAGGTCACAATGACTTGCAGGGCCAGCTCAAG
              10        20        30        40        50        60

V   S   Y   M   H   W   Y   Q   Q   K   P   G   S   S   P   K   P   W   I   Y
       TGTAAGTTACATGCACTGGTACCAGCAGAAGCCAGGATCCTCCCCCAAACCCTGGATTTA
              70        80        90       100       110       120

A   T   S   N   L   A   S   G   V   P   A   R   F   S   G   S   G   S   G   T
       TGCCACATCCAACCTGGCTTCTGGAGTCCCTGCTCGCTTCAGTGGCAGTGGGTCTGGGAC
             130       140       150       160       170       180

S   Y   S   L   T   I   I   R   V   E   A   E   D   A   A   T   Y   Y   C   Q
       CTCTTACTCTCTCACAATCATCAGAGTGGAGGCTGAAGATGCTGCCACTTATTACTGCCA
             190       200       210       220       230       240

Q   W   S   S   N   P   L   T   F   G   A   G   T   K   L   E   I
       GCAGTGGAGTAGTAACCCGCTCACGTTCGGTGCTGGGACCAAGCTGGAGATC
             250       260       270       280       290
```

```
  L   Q   E   S   G   P   D   L   V   K   P   S   Q   S   L   S   L   T   C   T
CTGCAGGAGTCAGGACCTGACCTGGTGAAACCTTCTCAGTCACTTTCACTCACCTGCACT
        10        20        30        40        50        60

V   T   G   Y   S   I   T   S   G   Y   S   W   H   W   I   R   Q   F   P   G
GTCACTGGCTACTCCATCACCAGTGGTTATAGCTGGCACTGGATCCGGCAGTTTCCAGGA
        70        80        90       100       110       120

N   K   L   E   W   M   G   Y   I   Q   Y   S   G   I   T   N   Y   N   P   S
AACAAACTGGAATGGATGGGCTACATACAGTACAGTGGTATCACTAACTACAACCCCTCT
       130       140       150       160       170       180

L   K   S   R   I   S   I   T   R   D   T   S   K   N   Q   F   F   L   Q   L
CTCAAAAGTCGAATCTCTATCACTCGAGACACATCCAAGAACCAGTTCTTCCTGCAGTTG
       190       200       210       220       230       240

N   S   V   T   T   E   D   T   A   T   Y   Y   C   A   R   E   D   Y   D   Y
AATTCAGTGACTACTGAGGACACAGCCACATATTACTGTGCAAGAGAAGACTATGATTAC
       250       260       270       280       290       300

H   W   Y   F   D   V   W   G   A   G   T   T   V   T   V   S   S
CACTGGTACTTCGATGTCTGGGGCGCAGGGACCACGGTCACCGTCTCCTCA
       310       320       330       340       350
```

```
  L   T   Q   S   P   A   I   M   S   A   S   L   G   E   E   I   T   L   T   C
CTGACCCAGTCTCCAGCAATCATGTCTGCATCTCTAGGGGAGGAGATCACCCTAACCTGC
        10        20        30        40        50        60

S   T   S   S   S   V   S   Y   M   H   W   Y   Q   Q   K   S   G   T   S   P
AGTACCAGCTCGAGTGTAAGTTACATGCACTGGTACCAGCAGAAGTCAGGCACTTCTCCC
        70        80        90       100       110       120

K   L   L   I   Y   S   T   S   N   L   A   S   G   V   P   S   R   F   S   G
AAACTCTTGATTTATAGCACATCCAACCTGGCTTCTGGAGTCCCTTCTCGCTTCAGTGGC
       130       140       150       160       170       180

S   G   S   G   T   F   Y   S   L   T   I   S   S   V   E   A   E   D   A   A
AGTGGGTCTGGGACCTTTTATTCTCTCACAATCAGCAGTGTGGAGGCTGAAGATGCTGCC
       190       200       210       220       230       240

D   Y   Y   C   H   Q   W   S   S   Y   P   T   F   G   G   G   T   K   L   E
GATTATTACTGCCATCAGTGGAGTAGTTATCCCACGTTCGGAGGGGGGACCAAGCTGGAG
       250       260       270       280       290       300
```

```
  Q   V   Q   L   Q   Q   S   G   P   E   L   V   K   P   G   A   S   V   K   M
CAGGTCCAACTGCAGCAGTCTGGACCTGAGCTGGTAAAGCCTGGGGCTTCAGTGAAGATG
         10        20        30        40        50        60

S   C   K   A   S   G   Y   T   F   T   Y   Y   V   I   H   W   V   K   Q   K
TCCTGCAAGGCTTCTGGATACACATTCACTTACTATGTTATTCACTGGGTGAAACAGAAG
         70        80        90       100       110       120

P   G   Q   G   L   E   W   I   G   Y   I   H   P   Y   N   A   G   T   E   Y
CCTGGGCAGGGCCTTGAGTGGATTGGATACATTCATCCTTACAATGCTGGTACTGAGTAC
        130       140       150       160       170       180

N   E   K   F   K   G   K   A   T   L   T   S   D   K   S   S   S   T   A   Y
AATGAGAAGTTCAAAGGCAAGGCCACACTGACTTCAGACAAATCCTCCAGCACAGCCTAC
        190       200       210       220       230       240

M   E   L   S   S   L   T   S   E   D   S   A   V   Y   Y   C   S   M   G   R
ATGGAGCTCAGCAGCCTGACCTCTGAGGACTCTGCGGTCTATTACTGTTCAATGGGACGA
        250       260       270       280       290       300

G   G   D   Y   W   G   Q   G   T   T   V   T   V   S   S
GGGGGTGACTACTGGGGCCAAGGGACCACGGTCACCGTCTCCTCA
        310       320       330       340
```

```
  L   T   Q   S   P   A   I   M   S   A   S   P   G   E   K   V   T   M   T   C
CTGACCCAGTCTCCAGCAATTATGTCTGCATCTCCTGGGGAGAAGGTCACCATGACCTGC
        10        20        30        40        50        60

S   A   S   S   S   V   S   Y   M   H   W   Y   Q   Q   K   S   G   T   S   P
AGTGCCAGCTCAAGTGTAAGTTACATGCACTGGTACCAGCAGAAGTCAGGCACCTCCCCC
        70        80        90       100       110       120

K   R   W   I   Y   D   T   S   K   L   A   S   G   V   P   A   R   F   S   G
AAAAGATGGATTTATGACACATCCAAACTGGCTTCTGGAGTCCCTGCTCGCTTCAGTGGC
       130       140       150       160       170       180

S   G   S   G   T   S   Y   S   L   T   I   S   S   M   E   A   E   D   A   A
AGTGGGTCTGGGACCTCTTACTCTCTCACAATCAGCAGCATGGAGGCTGAAGATGCTGCC
       190       200       210       220       230       240

T   Y   Y   C   Q   Q   W   S   S   N   P   F   T   F   G   A   G   T   K   L
ACTTATTACTGCCAGCAGTGGAGTAGTAACCCATTCACGTTCGGCGCGGGGACCAAGCTG
       250       260       270       280       290       300
```

```
A   E   S   G   P   G   L   V   R   L   T   S   L   S   I   T   C   T   V   S
GCAGAGTCAGGGCCTGGCCTGGTGCGCCTCACGAGCCTGTCCATCACTTGCACTGTCTCT
       10        20        30        40        50        60

G   F   S   L   I   S   Y   G   V   H   W   V   R   Q   P   P   G   K   G   L
GGCTTTTCATTAATTAGTTATGGTGTACACTGGGTTCGCCAGCCTCCAGGAAAGGGTCTG
       70        80        90       100       110       120

E   W   L   G   V   I   W   A   G   G   S   T   N   Y   N   S   A   L   M   S
GAGTGGCTGGGAGTAATATGGGCAGGTGGAAGCACAAATTATAATTCGGCTCTCATGTCC
      130       140       150       160       170       180

R   L   S   I   S   K   D   N   S   K   S   Q   V   F   L   K   M   N   S   L
AGACTGAGCATCAGCAAAGACAACTCCAAGAGCCAAGTTTTCTTAAAAATGAACAGTCTG
      190       200       210       220       230       240

Q   T   G   D   T   A   I   Y   Y   C   A   R   G   G   D   D   Y   D   G   F
CAAACTGGTGACACAGCCATATACTACTGTGCCAGAGGGGGGGATGATTACGATGGGTTT
      250       260       270       280       290       300

A   Y   W   G   Q   G   T   T   V   T   V   S   S   G   E   S
GCTTACTGGGGCCAAGGGACCACGGTCACCGTCTCCTCAGGTGAGTCC
      310       320       330       340
```

```
  L   T   Q   S   P   S   S   L   A   V   S   A   G   E   K   V   T   M   S   C
CTGACCCAGTCTCCATCCTCCCTGGCTGTGTCAGCAGGAGAGAAGGTCACTATGAGCTGC
         10        20        30        40        50        60

K   S   S   Q   S   L   L   S   S   T   K   R   K   N   Y   L   A   W   Y   Q
AAATCCAGTCAGAGTCTGCTCAGCAGTACAAAGCGAAAGAACTACTTGGCTTGGTACCAG
         70        80        90       100       110       120

Q   K   P   G   Q   S   P   K   L   L   I   Y   W   A   S   T   R   E   S   G
CAGAAACCAGGTCAGTCTCCTAAACTACTGATCTACTGGGCATCCACTCGGGAATCTGGG
        130       140       150       160       170       180

Y   P   D   R   F   T   G   S   G   S   G   T   D   F   T   L   T   I   S   S
GTCCCTGATCGCTTCACAGGCAGTGGATCTGGGACAGATTTCACTCTCACCATCAGCAGT
        190       200       210       220       230       240

V   Q   A   E   D   L   A   V   Y   Y   C   K   Q   S   Y   N   L   R   A   F
GTGCAGGCTGAAGACCTGGCAGTTTATTACTGCAAACAATCTTATAATCTTCGGGCGTTC
        250       260       270       280       290       300

G   G   G   T   K   L   E   I   K
GGTGGAGGGACCAAGCTGGAGATCAAA
        310       320
```

FIG. 34

SEQUENCE LISTING

```
(1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (xi) SEQUENCE DESCRIPTION: SEQ ID NO:1:

Gly Gly Gly Gly Ser
1               5

(2) INFORMATION FOR SEQ ID NO:2:
```

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:2:

Gly Glu Ala Ala Pro Ala Ala Ala Pro Ala Ala Ala Ala Ala Gly Gly
1               5                  10                  15

(2) INFORMATION FOR SEQ ID NO:3:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

CTGCCGCCCC CGCAGCCGCA GCCGCAGGCG GCCAGGTCCA ACTGCAGGAG AGCGGTCCAG       60

G                                                                     61

(2) INFORMATION FOR SEQ ID NO:4:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

CGGGGATCCT ATAAATCTCT GGC                                              23

(2) INFORMATION FOR SEQ ID NO:5:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GCGGAAGCTT CGGGCATGCT AATCTTCTCT CTTGCAGAGC CCAAATCTTG TGACACACCT       60

CCCCCGTGCC CAAGGTGCCC AGGACAG                                          87

(2) INFORMATION FOR SEQ ID NO:6:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

CTGTCCTGGG CACCTTGGGC ACGGGGGAGG TGTGTCACAA GATTTGGGCT CTGCAAGAGA       60

GAAGATTAGC ATGCCCGAAG CTTCCGC                                          87

(2) INFORMATION FOR SEQ ID NO:7:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

CCTCTGCCCT GGGATCCACC GCTGTGCC                                    28

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AACCATCACG AATTCACAGG GGCC                                        24

(2) INFORMATION FOR SEQ ID NO:9:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Ser Asp Tyr Tyr Met
            20                  25                  30

Asn Trp Val Arg Gln Pro Pro Gly Lys Ala Leu Glu Trp Leu Gly Phe
        35                  40                  45

Ile Ser Asn Lys Pro Asn Gly His Thr Thr Glu Tyr Ser Ala Ser Val
50                  55                  60

Lys Gly Arg Phe Thr Ile Ser Arg Asp Asn Ser Gln Ser Ile Leu Tyr
65                  70                  75                  80

Leu Gln Met Asn Thr Leu Arg Ala Glu Asp Ser Ala Thr Tyr Tyr Cys
                85                  90                  95

Ala Arg Asp Lys Gly Ile Arg Trp Tyr Phe Asp Val Trp Gly Gln Gly
            100                 105                 110

Thr Thr Val Thr Val Ser Ser
            115

(2) INFORMATION FOR SEQ ID NO:10:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CAGGTCCAAC TGCAGGAGTC TGGAGGAGGC TTGGTACAGC CTGGGGGTTC TCTGAGACTC    60

```
TCCTGCGCAA CTTCTGGGTT CAGTGATTAC TACATGAACT GGGTCCGCCA GCCTCCAGGA      120

AAAGCACTTG AGTGGTTGGG TTTTATTTCA AACAAACCTA ATGGTCACAC AACAGAGTAC      180

AGTGCATCTG TGAAGGGTCG GTTCACCATC TCCAGAGATA ATTCCCAAAG CATCCTCTAT      240

CTTCAAATGA ACACCCTGAG AGCTGAGGAC AGTGCCACTT ATTATTGTGC AAGAGATAAG      300

GGAATACGAT GGTACTTCGA TGTCTGGGGC CAAGGGACCA CGGTCACCGT CTCCTCA        357
```

(2) INFORMATION FOR SEQ ID NO:11:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Ala Ile Leu Ser Ala Ser Pro Gly Glu Lys Val Thr Met Thr Cys Arg
 1               5                  10                  15

Ala Ser Ser Ser Val Ser Tyr Met His Trp Tyr Gln Gln Lys Pro Gly
            20                  25                  30

Ser Ser Pro Lys Pro Trp Ile Tyr Ala Thr Ser Asn Leu Ala Ser Gly
        35                  40                  45

Val Pro Ala Arg Phe Ser Gly Ser Gly Ser Gly Thr Ser Tyr Ser Leu
 50                  55                  60

Thr Ile Ile Arg Val Glu Ala Glu Asp Ala Ala Thr Tyr Tyr Cys Gln
 65                  70                  75                  80

Gln Trp Ser Ser Asn Pro Leu Thr Phe Gly Ala Gly Thr Lys Leu Glu
            85                  90                  95

Ile
```

(2) INFORMATION FOR SEQ ID NO:12:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
AGCAATCCTG TCTGCATCTC CAGGGGAGAA GGTCACAATG ACTTGCAGGG CCAGCTCAAG      60

TGTAAGTTAC ATGCACTGGT ACCAGCAGAA GCCAGGATCC TCCCCCAAAC CCTGGATTTA      120

TGCCACATCC AACCTGGCTT CTGGAGTCCC TGCTCGCTTC AGTGGCAGTG GGTCTGGGAC      180

CTCTTACTCT CTCACAATCA TCAGAGTGGA GGCTGAAGAT GCTGCCACTT ATTACTGCCA      240

GCAGTGGAGT AGTAACCCGC TCACGTTCGG TGCTGGGACC AAGCTGGAGA TC            292
```

(2) INFORMATION FOR SEQ ID NO:13:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Leu Gln Glu Ser Gly Pro Asp Leu Val Lys Pro Ser Gln Ser Leu Ser

```
              1               5                  10                   15
Leu Thr Cys Thr Val Thr Gly Tyr Ser Ile Thr Ser Gly Tyr Ser Trp
                20                  25                  30

His Trp Ile Arg Gln Phe Pro Gly Asn Lys Leu Glu Trp Met Gly Tyr
                35                  40                  45

Ile Gln Tyr Ser Gly Ile Thr Asn Tyr Asn Pro Ser Leu Lys Ser Arg
        50                  55                  60

Ile Ser Ile Thr Arg Asp Thr Ser Lys Asn Gln Phe Phe Leu Gln Leu
65                  70                  75                  80

Asn Ser Val Thr Thr Glu Asp Thr Ala Thr Tyr Tyr Cys Ala Arg Glu
                85                  90                  95

Asp Tyr Asp Tyr His Trp Tyr Phe Asp Val Trp Gly Ala Gly Thr Thr
            100                 105                 110

Val Thr Val Ser Ser
            115
```

(2) INFORMATION FOR SEQ ID NO:14:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
CTGCAGGAGT CAGGACCTGA CCTGGTGAAA CCTTCTCAGT CACTTTCACT CACCTGCACT    60
GTCACTGGCT ACTCCATCAC CAGTGGTTAT AGCTGGCACT GGATCCGGCA GTTTCCAGGA   120
AACAAACTGG AATGGATGGG CTACATACAG TACAGTGGTA TCACTAACTA CAACCCCTCT   180
CTCAAAAGTC GAATCTCTAT CACTCGAGAC ACATCCAAGA ACCAGTTCTT CCTGCAGTTG   240
AATTCAGTGA CTACTGAGGA CACAGCCACA TATTACTGTG CAAGAGAAGA CTATGATTAC   300
CACTGGTACT TCGATGTCTG GGGCGCAGGG ACCACGGTCA CCGTCTCCTC A           351
```

(2) INFORMATION FOR SEQ ID NO:15:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Leu Thr Gln Ser Pro Ala Ile Met Ser Ala Ser Leu Gly Glu Glu Ile
1               5                   10                  15

Thr Leu Thr Cys Ser Thr Ser Ser Val Ser Tyr Met His Trp Tyr
                20                  25                  30

Gln Gln Lys Ser Gly Thr Ser Pro Lys Leu Leu Ile Tyr Ser Thr Ser
            35                  40                  45

Asn Leu Ala Ser Gly Val Pro Ser Arg Phe Ser Gly Ser Gly Ser Gly
        50                  55                  60

Thr Phe Tyr Ser Leu Thr Ile Ser Ser Val Glu Ala Glu Asp Ala Ala
65                  70                  75                  80

Asp Tyr Tyr Cys His Gln Trp Ser Ser Tyr Pro Thr Phe Gly Gly Gly
                85                  90                  95

Thr Lys Leu Glu
```

100

(2) INFORMATION FOR SEQ ID NO:16:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CTGACCCAGT CTCCAGCAAT CATGTCTGCA TCTCTAGGGG AGGAGATCAC CCTAACCTGC    60

AGTACCAGCT CGAGTGTAAG TTACATGCAC TGGTACCAGC AGAAGTCAGG CACTTCTCCC   120

AAACTCTTGA TTTATAGCAC ATCCAACCTG GCTTCTGGAG TCCCTTCTCG CTTCAGTGGC   180

AGTGGGTCTG GGACCTTTTA TTCTCTCACA ATCAGCAGTG TGGAGGCTGA AGATGCTGCC   240

GATTATTACT GCCATCAGTG GAGTAGTTAT CCCACGTTCG GAGGGGGGAC CAAGCTGGAG   300
```

(2) INFORMATION FOR SEQ ID NO:17:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gln Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Tyr Tyr
            20                  25                  30

Val Ile His Trp Val Lys Gln Lys Pro Gly Gln Gly Leu Glu Trp Ile
        35                  40                  45

Gly Tyr Ile His Pro Tyr Asn Ala Gly Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Met Gly Arg Gly Gly Asp Tyr Trp Gly Gln Gly Thr Thr Val Thr
            100                 105                 110

Val Ser Ser
        115
```

(2) INFORMATION FOR SEQ ID NO:18:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CAGGTCCAAC TGCAGCAGTC TGGACCTGAG CTGGTAAAGC CTGGGGCTTC AGTGAAGATG    60

TCCTGCAAGG CTTCTGGATA CACATTCACT TACTATGTTA TTCACTGGGT GAAACAGAAG   120

CCTGGGCAGG GCCTTGAGTG GATTGGATAC ATTCATCCTT ACAATGCTGG TACTGAGTAC   180
```

```
AATGAGAAGT TCAAAGGCAA GGCCACACTG ACTTCAGACA AATCCTCCAG CACAGCCTAC      240

ATGGAGCTCA GCAGCCTGAC CTCTGAGGAC TCTGCGGTCT ATTACTGTTC AATGGGACGA      300

GGGGGTGACT ACTGGGGCCA AGGGACCACG GTCACCGTCT CCTCA                      345
```

(2) INFORMATION FOR SEQ ID NO:19:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Leu Thr Gln Ser Pro Ala Ile Met Ser Ala Ser Pro Gly Glu Lys Val
1               5                   10                  15

Thr Met Thr Cys Ser Ala Ser Ser Val Ser Tyr Met His Trp Tyr
                20                  25                  30

Gln Gln Lys Ser Gly Thr Ser Pro Lys Arg Trp Ile Tyr Asp Thr Ser
            35                  40                  45

Lys Leu Ala Ser Gly Val Pro Ala Arg Phe Ser Gly Ser Gly Ser Gly
        50                  55                  60

Thr Ser Tyr Ser Leu Thr Ile Ser Ser Met Glu Ala Glu Asp Ala Ala
65                  70                  75                  80

Thr Tyr Tyr Cys Gln Gln Trp Ser Ser Asn Pro Phe Thr Phe Gly Ala
                85                  90                  95

Gly Thr Lys Leu
            100
```

(2) INFORMATION FOR SEQ ID NO:20:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CTGACCCAGT CTCCAGCAAT TATGTCTGCA TCTCCTGGGG AGAAGGTCAC CATGACCTGC      60

AGTGCCAGCT CAAGTGTAAG TTACATGCAC TGGTACCAGC AGAAGTCAGG CACCTCCCCC     120

AAAAGATGGA TTTATGACAC ATCCAAACTG GCTTCTGGAG TCCCTGCTCG CTTCAGTGGC     180

AGTGGGTCTG GGACCTCTTA CTCTCTCACA ATCAGCAGCA TGGAGGCTGA AGATGCTGCC     240

ACTTATTACT GCCAGCAGTG GAGTAGTAAC CCATTCACGT TCGGCGCGGG GACCAAGCTG     300
```

(2) INFORMATION FOR SEQ ID NO:21:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Ala Glu Ser Gly Pro Gly Leu Val Arg Leu Thr Ser Leu Ser Ile Thr
1               5                   10                  15
```

```
Cys Thr Val Ser Gly Phe Ser Leu Ile Ser Tyr Gly Val His Trp Val
            20                  25                  30

Arg Gln Pro Pro Gly Lys Gly Leu Glu Trp Leu Gly Val Ile Trp Ala
            35                  40                  45

Gly Gly Ser Thr Asn Tyr Asn Ser Ala Leu Met Ser Arg Leu Ser Ile
        50                  55                  60

Ser Lys Asp Asn Ser Lys Ser Gln Val Phe Leu Lys Met Asn Ser Leu
65                  70                  75                  80

Gln Thr Gly Asp Thr Ala Ile Tyr Tyr Cys Ala Arg Gly Gly Asp Asp
                85                  90                  95

Tyr Asp Gly Phe Ala Tyr Trp Gly Gln Gly Thr Thr Val Thr Val Ser
            100                 105                 110

Ser Gly Glu Ser
        115

(2) INFORMATION FOR SEQ ID NO:22:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GCAGAGTCAG GGCCTGGCCT GGTGCGCCTC ACGAGCCTGT CCATCACTTG CACTGTCTCT      60

GGCTTTTCAT TAATTAGTTA TGGTGTACAC TGGGTTCGCC AGCCTCCAGG AAAGGGTCTG     120

GAGTGGCTGG GAGTAATATG GGCAGGTGGA AGCACAAATT ATAATTCGGC TCTCATGTCC     180

AGACTGAGCA TCAGCAAAGA CAACTCCAAG AGCCAAGTTT TCTTAAAAAT GAACAGTCTG     240

CAAACTGGTG ACACAGCCAT ATACTACTGT GCCAGAGGGG GGGATGATTA CGATGGGTTT     300

GCTTACTGGG GCCAAGGGAC CACGGTCACC GTCTCCTCAG GTGAGTCC                  348

(2) INFORMATION FOR SEQ ID NO:23:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Leu Thr Gln Ser Pro Ser Ser Leu Ala Val Ser Ala Gly Glu Lys Val
1               5                   10                  15

Thr Met Ser Cys Lys Ser Ser Gln Ser Leu Leu Ser Ser Thr Lys Arg
            20                  25                  30

Lys Asn Tyr Leu Ala Trp Tyr Gln Gln Lys Pro Gly Gln Ser Pro Lys
            35                  40                  45

Leu Leu Ile Tyr Trp Ala Ser Thr Arg Glu Ser Gly Tyr Pro Asp Arg
        50                  55                  60

Phe Thr Gly Ser Gly Ser Gly Thr Asp Phe Thr Leu Thr Ile Ser Ser
65                  70                  75                  80

Val Gln Ala Glu Asp Leu Ala Val Tyr Tyr Cys Lys Gln Ser Tyr Asn
                85                  90                  95

Leu Arg Ala Phe Gly Gly Gly Thr Lys Leu Glu Ile Lys
            100                 105
```

(2) INFORMATION FOR SEQ ID NO:24:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
CTGACCCAGT CTCCATCCTC CCTGGCTGTG TCAGCAGGAG AGAAGGTCAC TATGAGCTGC        60

AAATCCAGTC AGAGTCTGCT CAGCAGTACA AAGCGAAAGA ACTACTTGGC TTGGTACCAG       120

CAGAAACCAG GTCAGTCTCC TAAACTACTG ATCTACTGGG CATCCACTCG GGAATCTGGG       180

GTCCCTGATC GCTTCACAGG CAGTGGATCT GGGACAGATT TCACTCTCAC CATCAGCAGT       240

GTGCAGGCTG AAGACCTGGC AGTTTATTAC TGCAAACAAT CTTATAATCT TCGGGCGTTC       300

GGTGGAGGGA CCAAGCTGGA GATCAAA                                          327
```

TETRAVALENT BISPECIFIC RECEPTORS, THE PREPARATION AND USE THEREOF

This application is a continuation, of application Ser. No 08/109,986 filed Aug. 23, 1993, now abandoned, which is a continuation of application Ser. No. 07/891,739, filed Jun. 1, 1992, abandoned.

BACKGROUND OF THE INVENTION

The invention relates to tetravalent bispecific receptors which are prepared by genetic manipulation by fusion of the DNA which codes for the heavy chain of an F(ab')2 fragment of an antibody (I) with (a) DNA which codes for the heavy chain of an F(ab')2 molecule of a second antibody (II), in which the CH1 domain is replaced by a CH3 domain (formula I), or with (b) the DNA which codes for a single chain FV fragment of an antibody (II) (formula II), by means of suitable linkers. The expression of these fusion genes in mammalian cells together with the genes for the corresponding light chains, which in the case of the construct (a) are composed on the one hand of a VL exon of specificity I and a CK exon, and on the other hand of a VL exon of specificity II and a CH3 exon, and in the case of the construct (b) only of a VL exon of specificity I and a CK exon, yields tetravalent bispecific receptors. In this case the CH1 domains are connected to the VH2 domains via 1 to 10 hinge regions (H) and a suitable peptide linker L. The antibody specificities described in European Patent Application EP-A2-0404 097 are preferably employed. They are, inter alia, on the one hand specificities which are directed against an epitope, which is located on the cell membrane or in the interstitium of a tumor-associated antigen. On the other hand, these are specificities which are directed against high or low molecular weight ligands which in turn bind an agent which is active against tumors, or bind this active agent directly.

EP-A2-0404 097 describes bispecific and oligospecific, mono- and oligovalent receptors which are prepared by genetic manipulation by fusion of DNA coding for F(ab) fragments of antibodies of two or more different specificities by means of suitable linkers. In this case, one specificity is; preferably directed either against an epitope, which, is located on the cell membrane or in the interstitium, of a tumor-associated antigen (TAA) or against an epitope in the tumor endothelium (TE), while the other specificities relate to high or low molecular weight ligands and react, for example, with the complexons ethylenediaminetetraacetate and diethylenetriaminepentaacetate in yttrium-90-complexed form (EDTA-90Y and DTPA-90Y respectively). In a particularly preferred embodiment, the binding to the complexons takes place on the complexon receptor arm via fos-jun interaction (or else avidin-biotin interaction). Other preferred specificities have catalytic properties.

DESCRIPTION OF RELATED ART

Bispecific antibodies have hitherto been prepared by the following methods
- chemical coupling of antibodies of different specificity via heterobifunctional linkers (H. Paulus, Behring Inst. Mitt. 78, (1985), 118–132)
- fusion of hybrids which are already available and which secrete different monoclonal antibodies (MAbs), and isolation of the bispecific monovalent portion (U.S. Staerz and M. J. Bevan, Proc. Natl. Acad. Sci. USA 83, (1986) 1453–1457)
- transfection of the light and heavy chain genes of two different MAbs (4 genes) into murine myeloma cells or other eukaryotic expression systems and isolation of the bispecific monovalent portion (U. Zimmermann, Rev. Physio. Biochem. Pharmacol. 105 (1986), 176–260; J. van Dijk et al., Int. J. Cancer 43, (1989), 944–349).

SUMMARY OF THE INVENTION

Such bispecific antibodies are employed for the therapy and diagnosis of malignant tumors. The principle of the method comprises in the first step a saturation of the epitopes on the target cells which are recognized by one of the two specificities on by multiple high dose injections of the bispecific macromolecule. In the second step, which comprises interruption of the treatment for several days, autoelimination of the non-specifically adsorbed bispecific antibodies from the non-target tissues takes place.

This autoelimination can be speeded up by injection of an anti-idiotype antibody which is coupled to sugar residues, preferably galactose, and which is directed against the anti-tumor arm of the bispecific receptor.

The third step in the method comprises i.v. injection of a radiolabeled, hydrophilic, low molecular weight ligand which does not accumulate in cells, has a short residence time in the body, has high complexation constants for beta- and gamma-emitters such as 90Y, 186Re, 188Re, 189Re, 99mTc or 111In and binds with high affinity to the second specificity of the bispecific antibody. This step achieves accumulation of the radioactive ligand, together with a longer residence on the target tissue, which results in the selective destruction of the target tissue or makes diagnosis possible, for example of metastases.

We have found that tetravalent bispecific receptors of the formula I or formula II can be prepared particularly well by genetic manipulation because they are expressed considerably more efficiently than bispecific antibodies generated by other methods. An additional factor is that the avidity of the original antibodies for their corresponding antigens is retained in the constructs according to the invention. Preferred constructs have 1 to 5, very preferably 1, hinge region between CH1 and VH2, because such constructs are expressed particularly efficiently in BHK cells. Preferably employed as linkers are the sequences corresponding to the peptide sequence (Gly-Gly-Gly-Gly-Ser)x (SEQ ID NO:1) with x=3 to 5 or GEAAPAAAPAAAAAGG (SEQ ID NO:2). Otherwise, the antibody V gene fragments or specificities described or preferred in the abovementioned EP-A2-0404 097 are also preferably employed in this case.

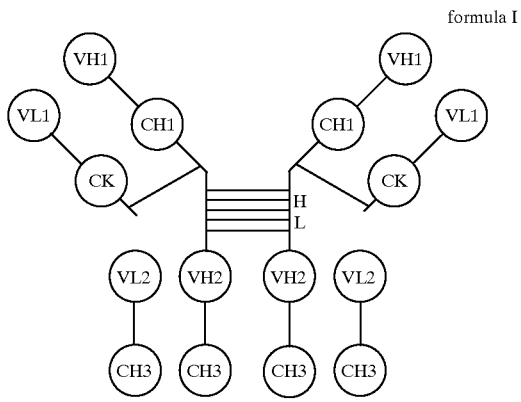

formula I

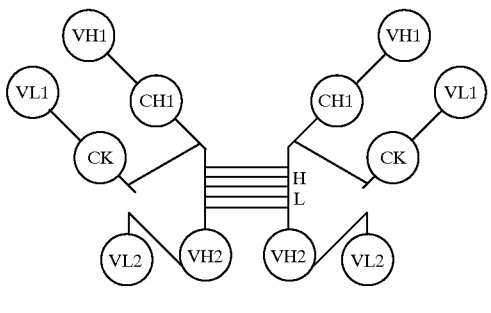

formula II

H = hinge
L = linker
━ = peptide linkage
─── = dilsulfide bridge

The construction of a fusion gene which codes for a tetravalent bispecific receptor molecule is described by way of example hereinafter. Unless otherwise noted, the techniques used for this are taken from the book "Molecular Cloning: A Laboratory Manual" (T. Maniatis et al., 1989). Further details are described in EP-A2-0404 097, to which particular reference is made here.

The present invention accordingly relates to bispecific tetravalent receptors of the formula I or formula II, to processes for the preparation thereof and to the use thereof. It is preferable for one specificity to be directed against animal or human tumor-specific antigens and the other specificity to have catalytic or enzymatic activity or be directed against a completing agent. In another preferred embodiment, one specificity derives from the monoclonal antibodies with the variable regions shown in Tab. 2, 3, 4 or 5 in EP-A2-0404 097. The variable regions disclosed in Tab. 2, 3, 4, and 5 of European application 0 404 097 are present in FIGS. 27–34.

DESCRIPTION OF SPECIFIC EMBODIMENTS

EXAMPLE 1

Figure 1:
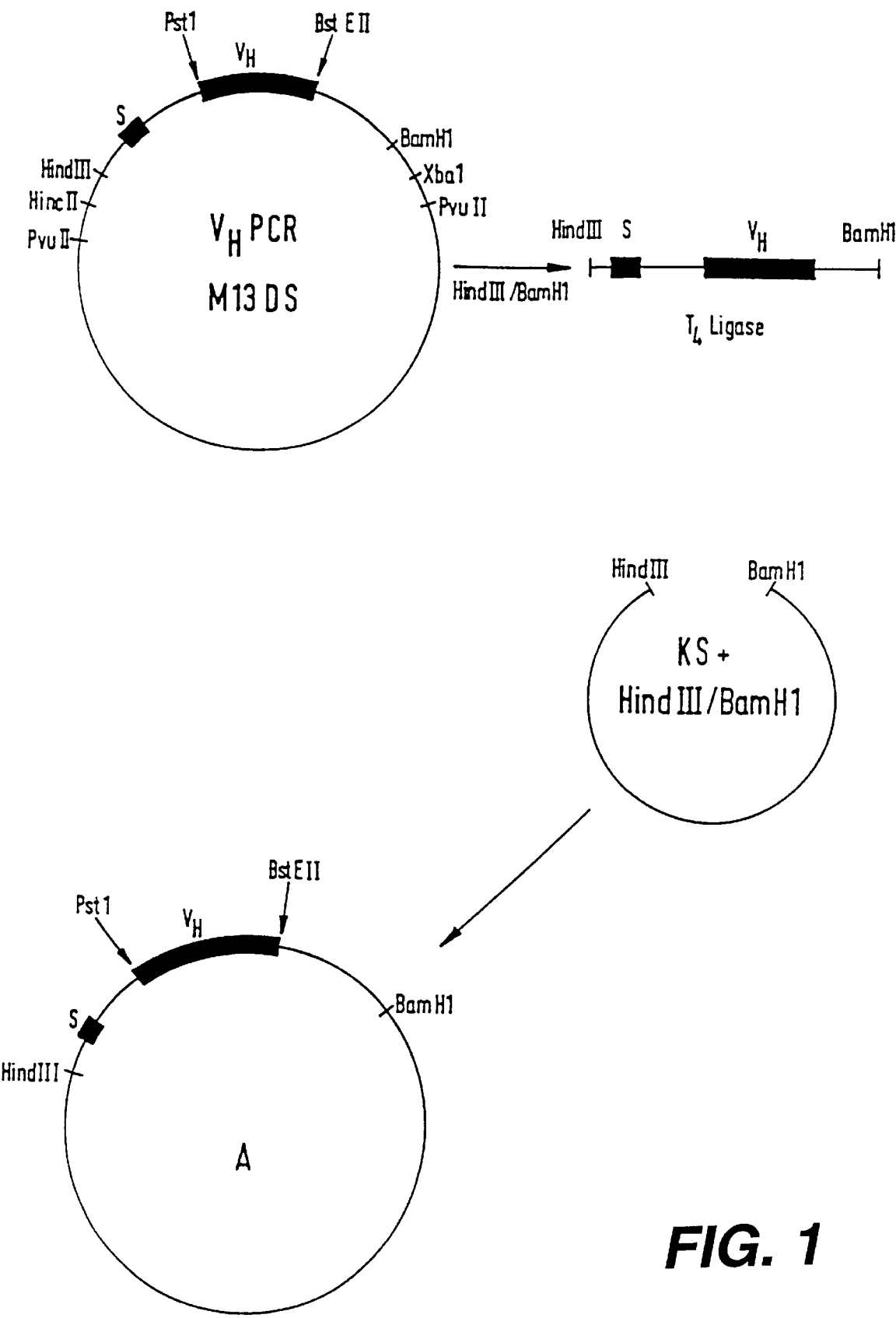

A derivative of an M13 phage (VH PCR) which contains the 5' part of a heavy chain gene composed of promoter region, signal exon, intron 1, VH exon and intron 2 (R. Orlandi et al., Proc. Natl. Acad. Sci. USA, Vol. 86, 3833–3837, 1988) was cleaved with the restriction endonucleases HindIII and BamHI, and the insert was isolated and cloned into a HindIII/BamHI-cleaved KS+ phasmid (pBluescript KSR+, Stratagene LaJolla, Calif., USA). The phasmid clone (A) which contains the insert cut out of the VH PCR was identified by restriction analysis and nucleic acid sequence analysis (FIG. 1).

EXAMPLE 2

Figure 2:
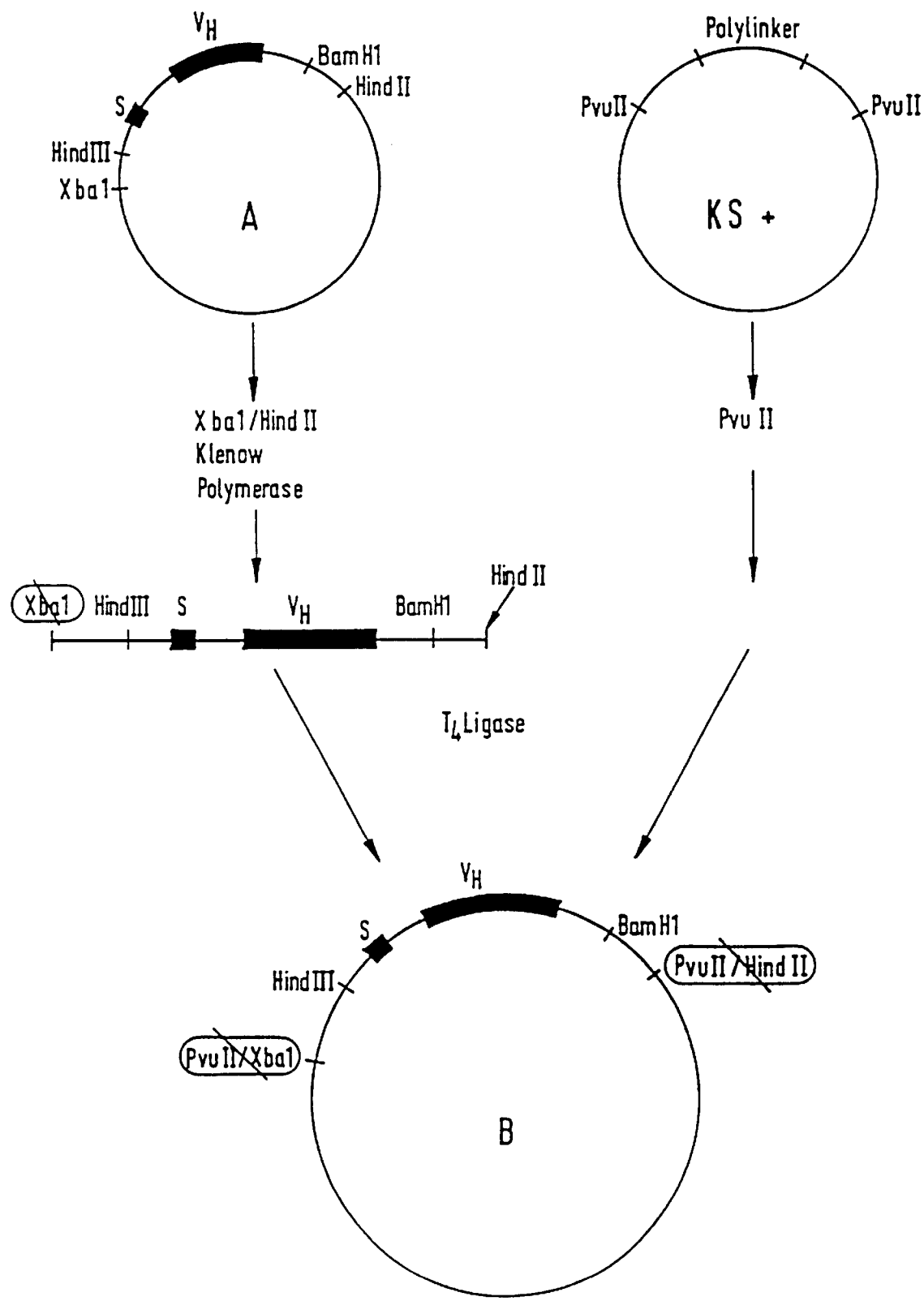

The phasmid clone (A) was cleaved with XbaI and HindII, the XbaI cleavage site was made blunt ended using polymerase and dNTPs, and the DNA fragment with the V gene exon was isolated. The isolated DNA fragment was then cloned into a KS+ phasmid from which the polylinker and the regions adjacent to the polylinker had been deleted by PvuII digestion. The clone (B) which contains the VH insert and the regions of the KS+ polylinker located between the XbaI and BamHI or HindII and HindIII cleavage sites was identified (FIG. 2). The phasmid B was used to clone the VH genes of the antibodies I and II (VH1 and VH2) after amplification from the cDNA of the hybrid cells. Amplification of the VH genes was carried out by the method described by R. Orlandi et al. (1989, loc. cit.). The phasmid clone B with the VH1 gene is called B1, and the phasmid clone B with the VH2 gene is called B2 (R. M. Hudziak et al., Cell., Vol. 31, 137–146, 1982; F. Lee et al., Nature, Vol. 294, 228, 1981).

EXAMPLE 3

Figure 3:
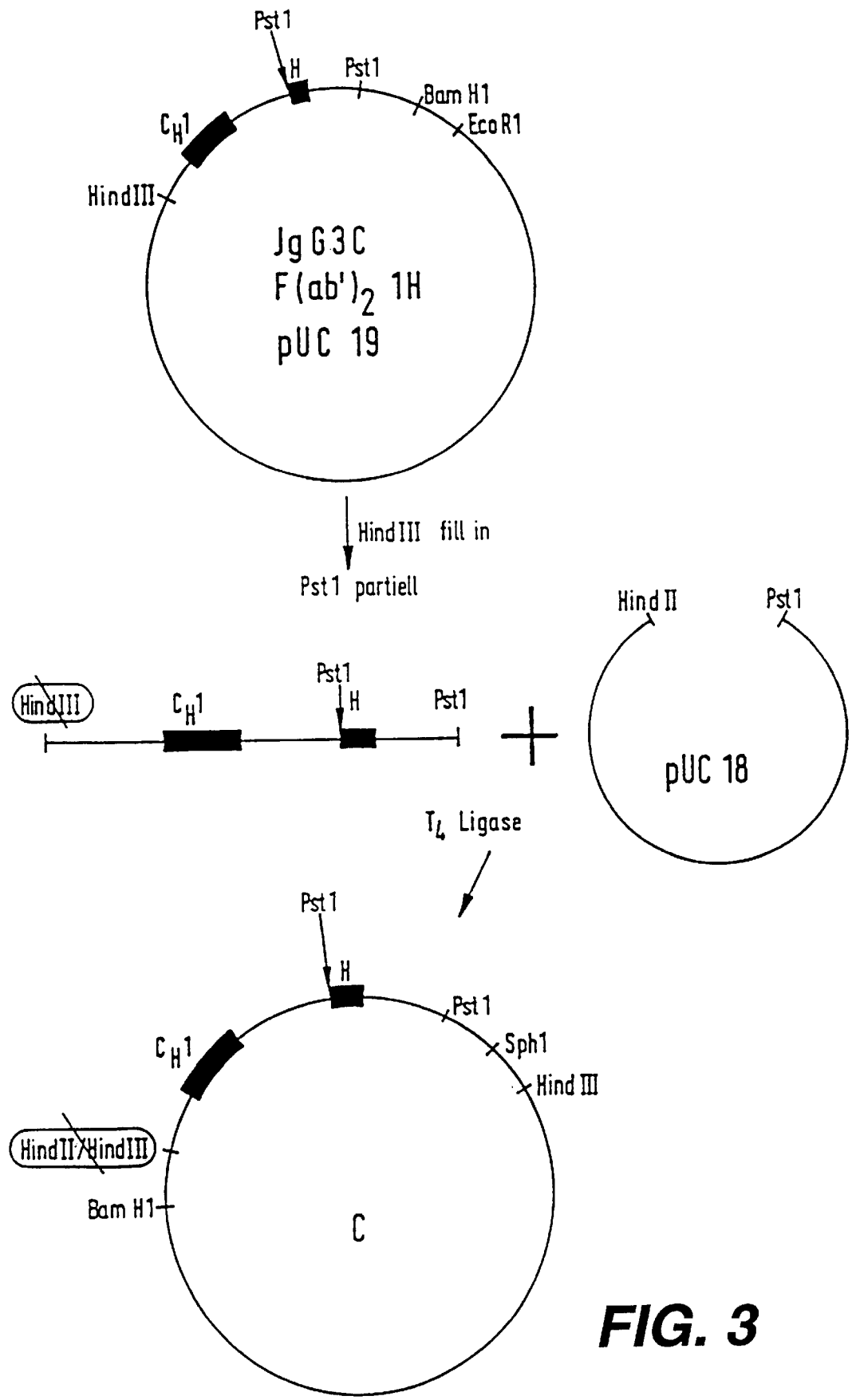

A pUC 19 plasmid which contains the CH1 exon and the first hinge exon of a human IgG3 gene (EP-A2-0404 097; FIG. 3 ibidem: IgG3 (F(ab')2 1H)), was cleaved with the restriction endonuclease HindIII, and the cleavage sites were made blunt ended with Klenow DNA polymerase. This was followed by partial cleavage with PstI, and the DNA fragment with the CH1 exon and the H1 exon was isolated and cloned into a pUC 18 plasmid cleaved with PstI and HindII. The clone (C) which harbors a BamHI cleavage site 5' of the insert and a HindIII cleavage site 3' of the insert was isolated (FIG. 3).

EXAMPLE 4

Figure 4:
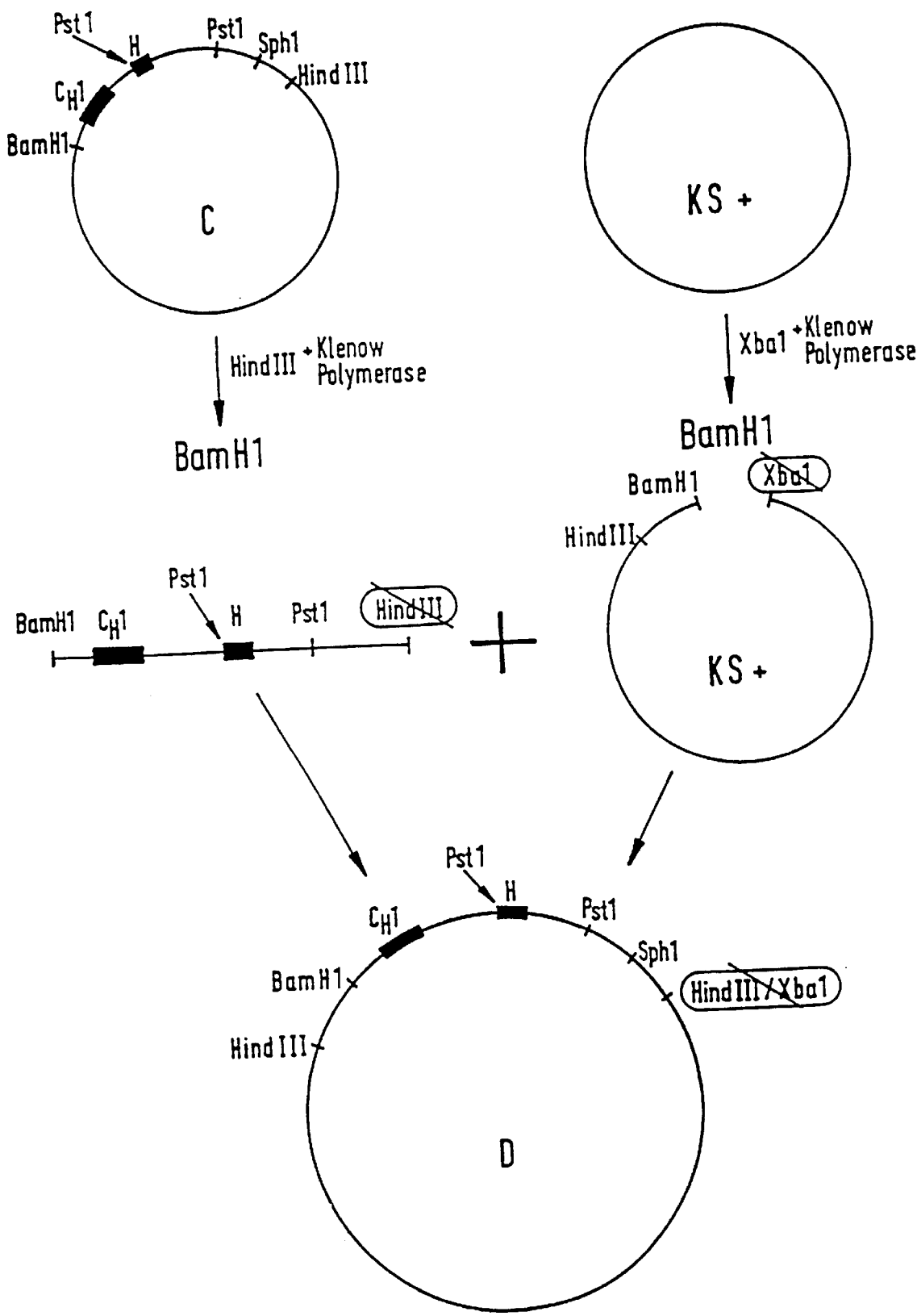

The plasmid clone C was cleaved with HindIII, and the cleavage sites were filled in with Klenow DNA polymerase. Then the insert with the CH1 and H1 exons was cut out with BamHI, isolated and cloned into a KS+ phasmid (pBluescriptR IIKS+, Stratagene, LaJolla, Calif., USA). The KS+ phasmid had been cleaved with XbaI, the XbaI cleavage sites made blunt ended in with Klenow DNA polymerase and subsequently cut with BamHI. The phasmid clone (D) which contains the insert with the CH1 and hinge 1 exons in an orientation in which a BamHI and a HindIII cleavage site are located on the 5' side of the insert was isolated (FIG. 4).

EXAMPLE 5

Figure 5:
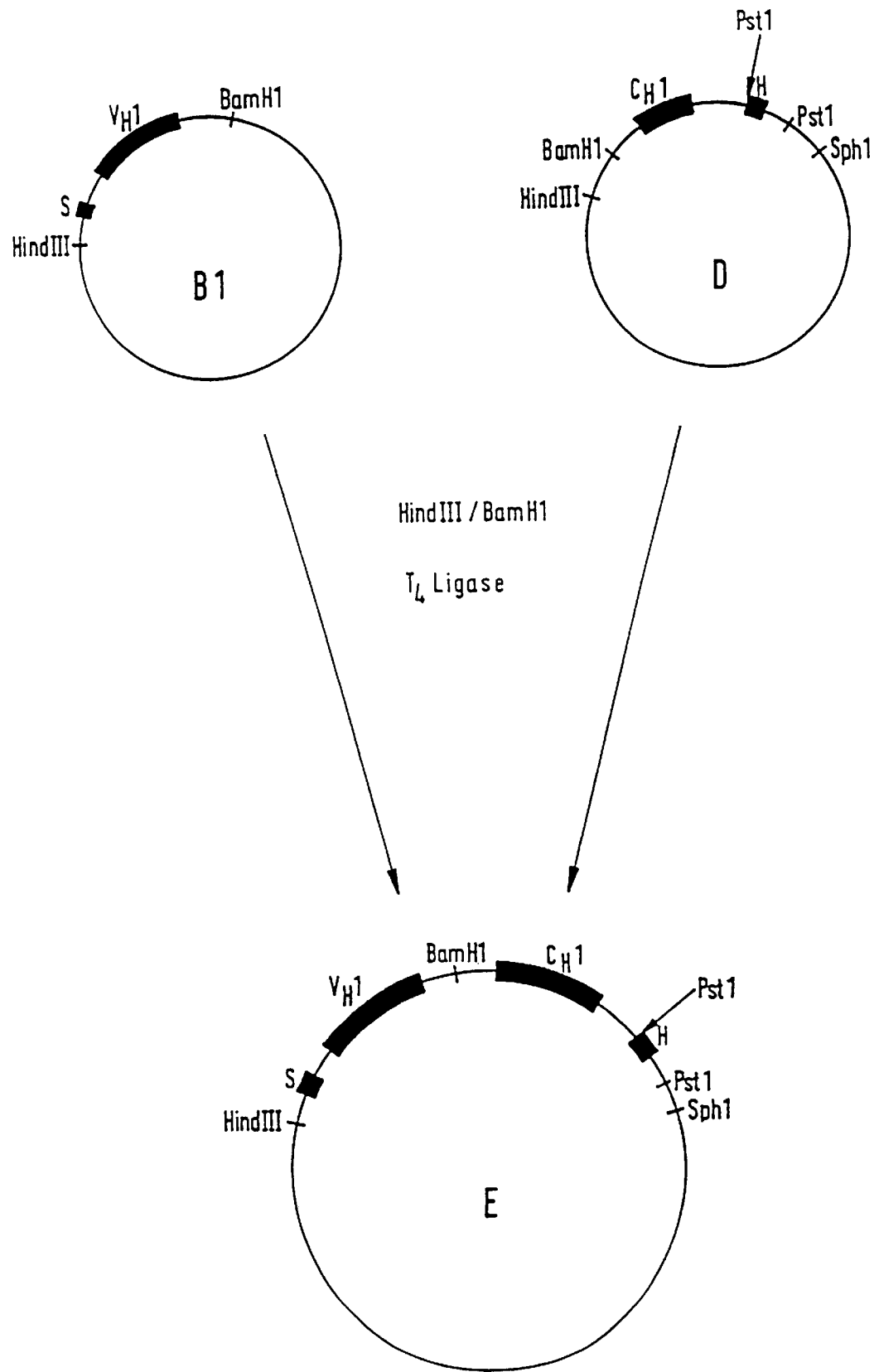

The phasmid clone (B1) was cleaved with HindIII and BamHI, and the insert with the VH gene of antibody I was isolated and cloned into the vector (D) which had likewise been cleaved with HindIII and BamHI. The clone (E) which contains the VH1 gene, the CH1 and the hinge 1 exon was isolated (FIG. 5).

EXAMPLE 6

A DNA fragment (F) which contains a VH gene extended by a linker and harbors at its 5' end a cleaved PvuII cleavage site and at its 3' end a BamHI cleavage site (FIG. 6) was; amplified from the phasmid vector B2 by the polymerase chain reaction (PCR) using the oligonucleotides VHOligoI and VHOligoII (Tab. 1) (SEQ ID NOS:3 and 4). This fragment was cleaved with BamHI and cloned into a BamHI/PvuII cleaved KS+ vector in which one of the two internal PvuII cleavage sites had previously been destroyed by Asp718/PvuII cleavage, filling-in of the cleavage sites and religation.

TABLE 1

(SEQ ID NO:3)
VH OligoI: _____

PvuII

5'         CT.GCC.GCC.CCC.GCA.GCC.GCA.

TABLE 1-continued

```
    GCC.GCA.GGC.GGC.CAG.GTC.CAA.CTG.CAG.GAG.
    AGC.GGT.CCA.GG
```

VH OligoII:                                       (SEQ ID NO:4)

```
         BamHI
5'                                          3'
    CGG.GGA.TCC.TAT.AAA.TCT.CTG.GC
```

Figure 6:
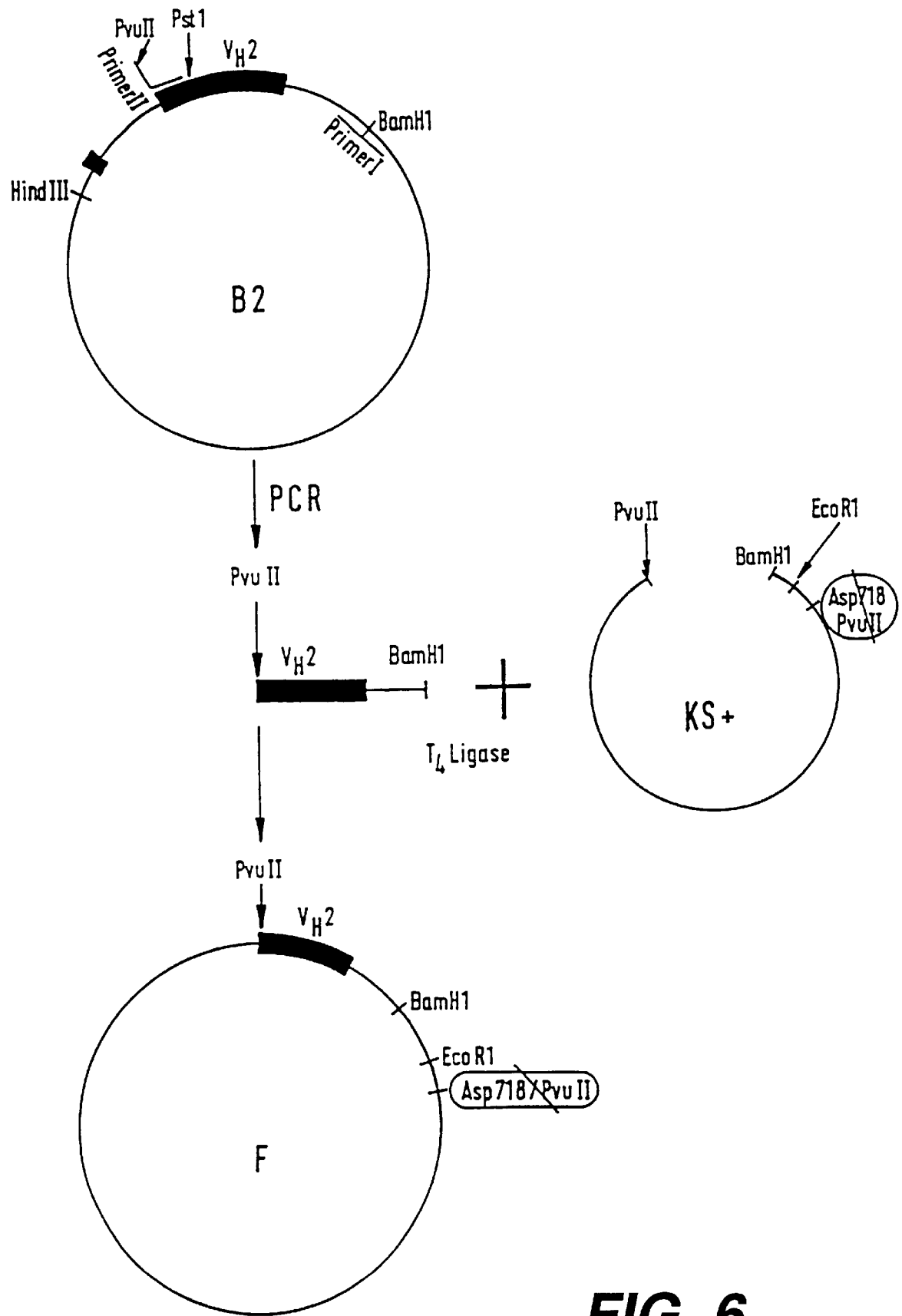

The phasmid clone (F) which contains the amplified fragment was isolated (FIG. 6).

EXAMPLE 7

Figure 7:
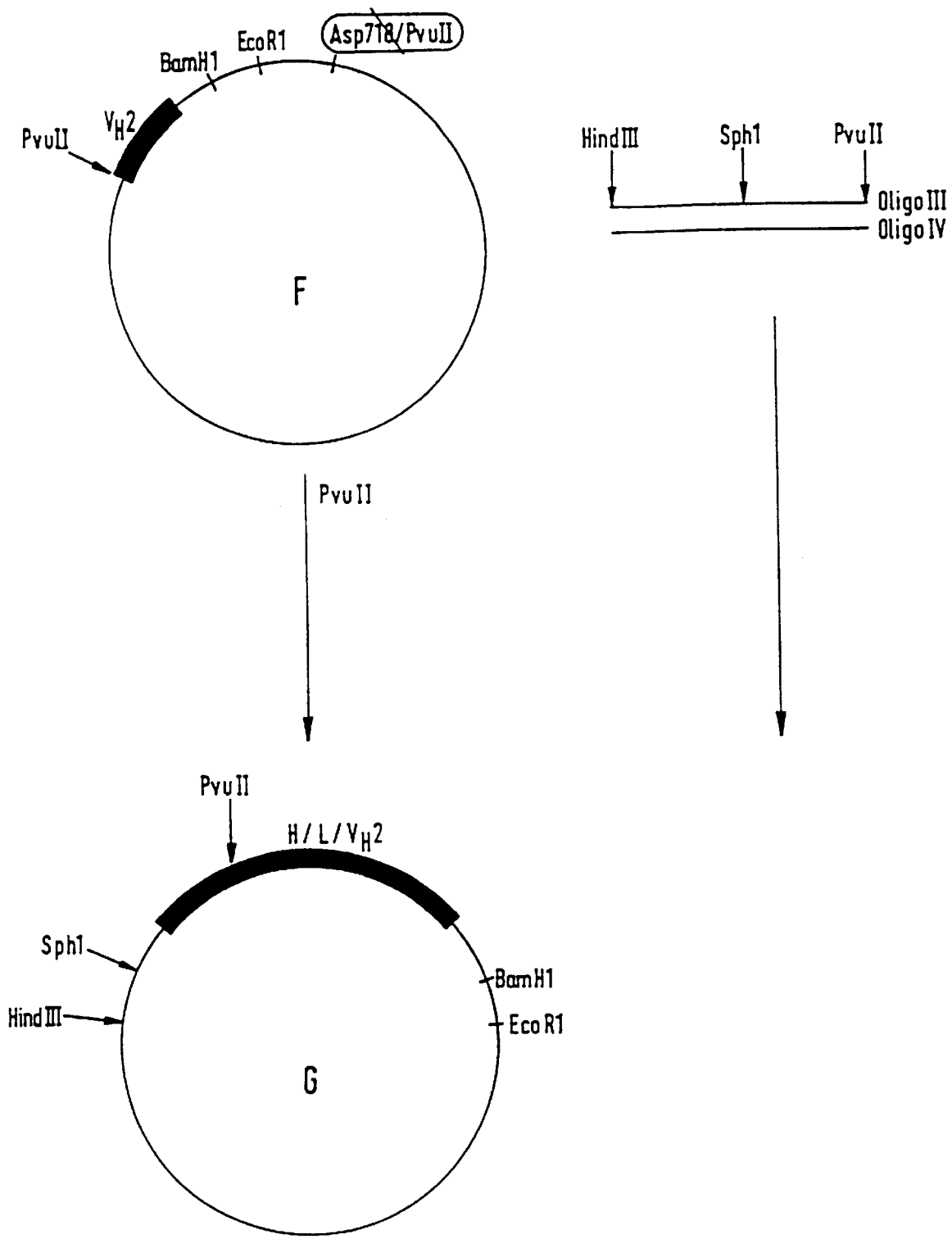

The oligonucleotides OligoIII and IV (Tab. 2) (SEQ ID NOS:5 and 6) were annealed together, and the resulting DNA fragment was ligated into the phasmid clone (F) cleaved with PvuII (FIG. 7). The phasmid clone (G) which contains a fusion exon composed of a hinge exon, an oligonucleotide linker and the VH2 gene was isolated.

TABLE 2

Oligo III:                                        (SEQ ID NO:5)

```
5'
      Hind III      Sph I
GCG.GAA.GCT.TCG.GGC.ATG.CTA.ATC.TTC.TCT.CTT.GCA.GAG.
CCC.AAA.TCT.TGT.GAC.ACA.CCT.CCC.CCG.TGC.CCA.AGG.TGC.
CCA.GGA.CAG 3'
```

Oligo IV:                                         (SEQ ID NO:6)

```
5'
CTG.TCC.TGG.GCA.CCT.TGG.GCA.CGG.GGG.AGG.TGT.GTC.ACA.
AGA.TTT.GGG.CTC.TGC.AAG.AGA.GAA.GAT.TAG.CAT.GCC.CGA.
AGC.TTC.CGC 3'                        Sph I
Hind III
```

EXAMPLE 8

Figure 8:
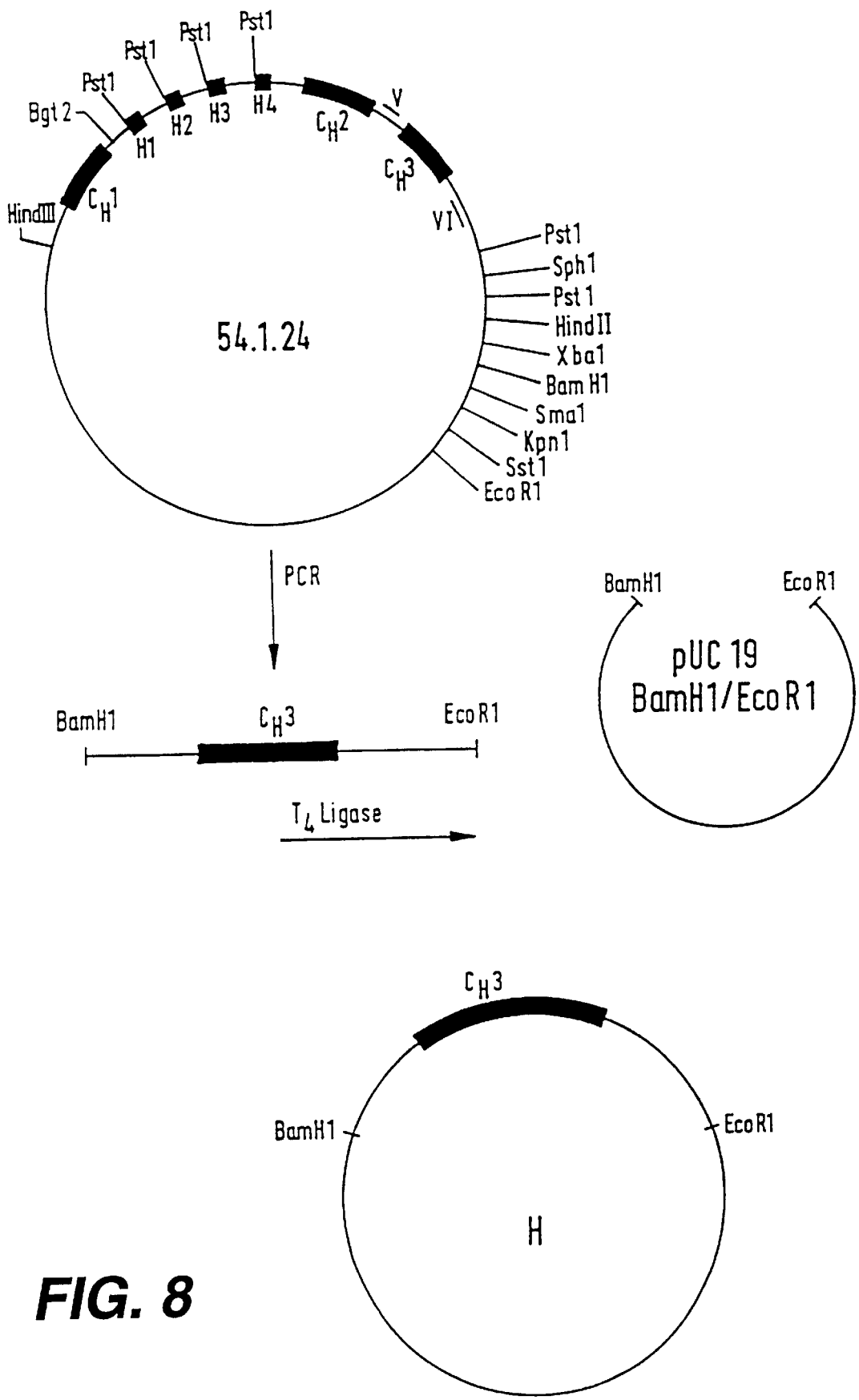
Figure 9:
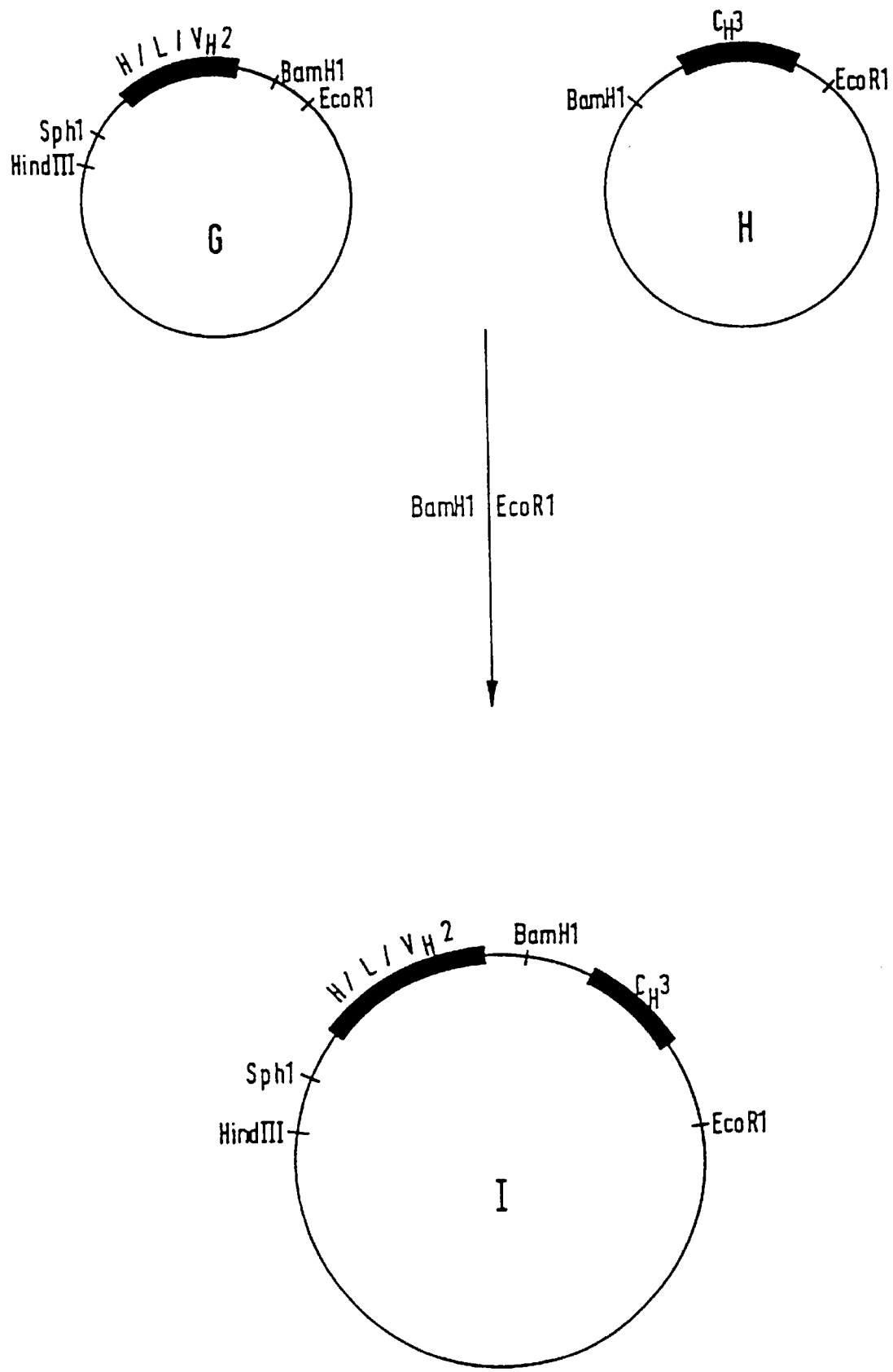

The CH3 exon and 3' NT region of the IgG3 gene were amplified out of the plasmid clone 54.1.24, which contains a human IgG3 C gene (EP-A2-0404 097, FIG. 2), with the oligonucleotides V and VI (Tab. 3) (SEQ ID NO:7 and 8) and cloned into the BamHI and EcoRI cleavage sites of a pUC 19 plasmid (FIG. 8). The plasmid clone (H) which contains the CH3 exon of the IgG3 gene was isolated.

TABLE 3

Oligo V:                                          (SEQ ID NO:7)

```
5'            BamHI
                                           3'
CC.TCT.GCC.CTG.GGA.TCC.ACC.GCT.GTG.CC
```

Oligo VI:

TABLE 3-continued (SEQ ID NO:8)
```
5'            EcoRI
                                           3'
AAC.CAT.CAC.GAA.TTC.ACA.GGG.GCC
```

EXAMPLE 9

The plasmid clone (H) was cleaved with BamHI and EcoRI, and the DNA fragment which harbors the CH3 exon was cloned into the phasmid clone (G) cleaved with BamHI and EcoRI (FIG. 3). The phasmid clone (I) which contains the hinge/linker,/VH2 fusion exon and the CH3 exon was isolated.

EXAMPLE 10

Figure 10:
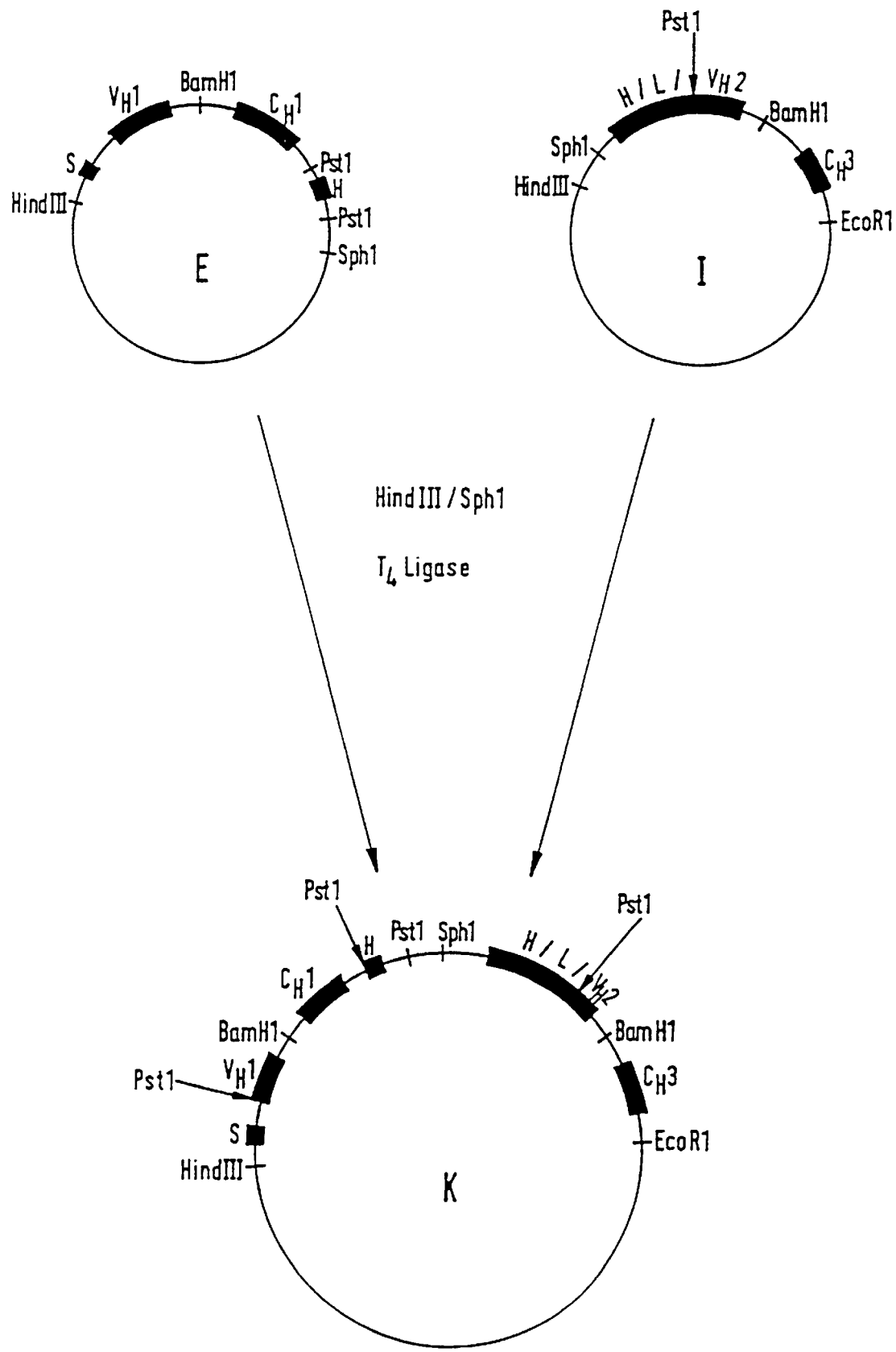

The phasmid clones (E) and (I) were cleaved with HindIII and SphI. The insert of the clone (E) was cloned into the HindIII and SphI cleavage sites of the phasmid clone (I). The phasmid clone (K) containing an Ig heavy chain fusion gene which is composed of signal exon, VH1 exon, CH1 exon, hinge 1 exon, hinge/linker/VH2 MAbII fusion exon and CH3 exon was isolated (FIG. 10).

EXAMPLE 11

Figure 11:
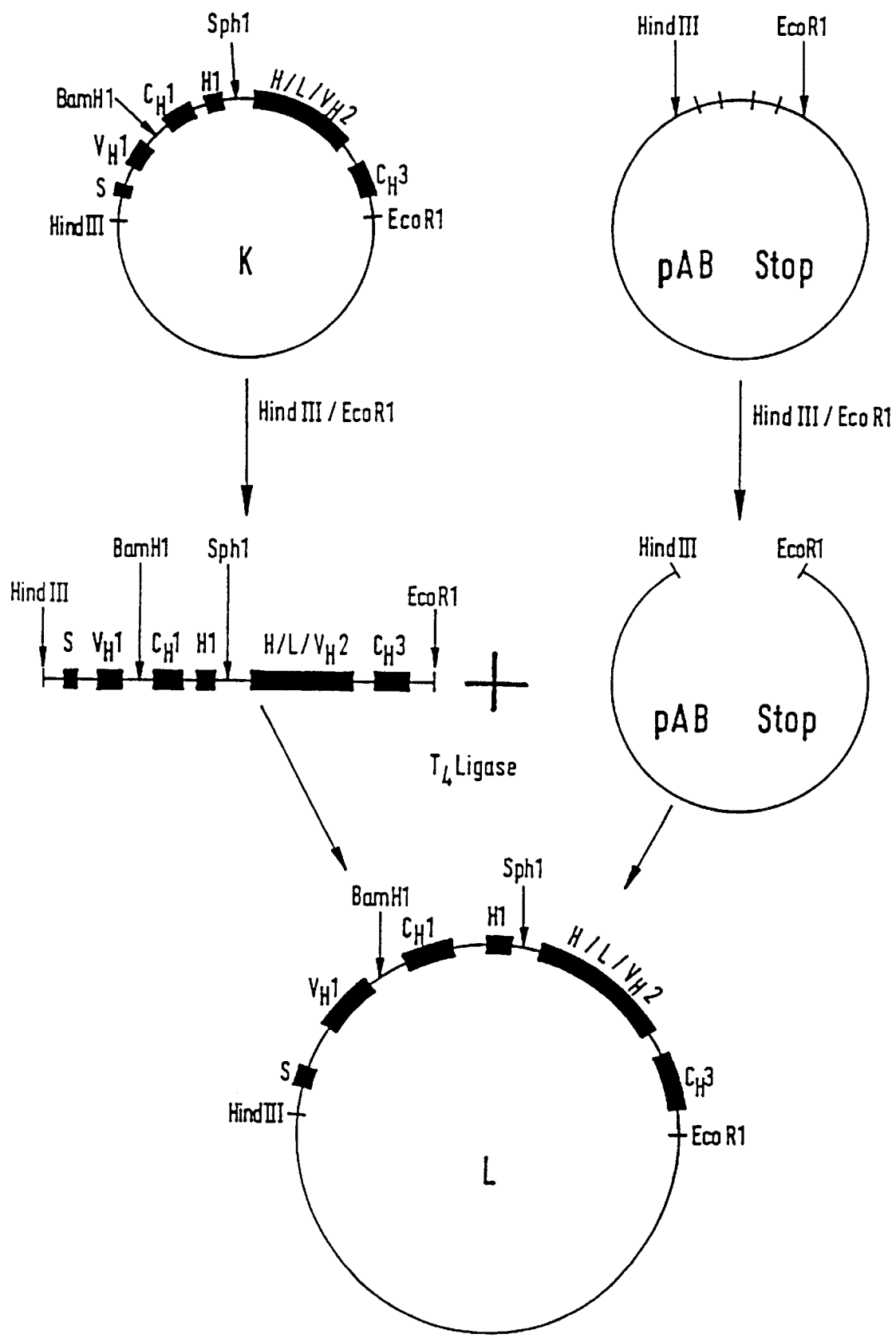
Figure 19:
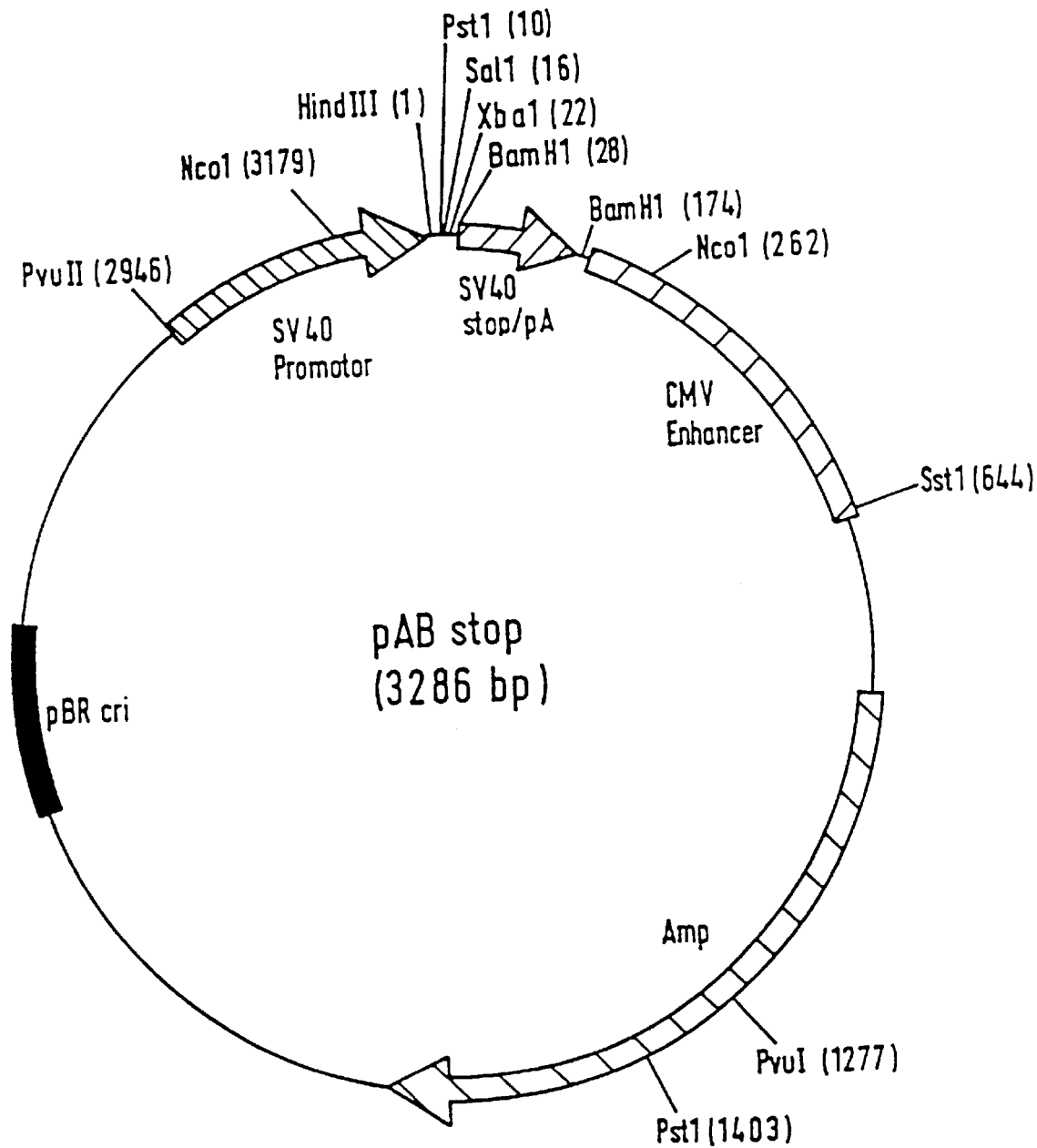

The HindIII-EcoRI fragment with the fusion gene was cut out of the phasmid clone (K) and cloned into a pAB Stop expression vector (FIG. 19, pAB Stop is a derivative of the pAB 3 vector (G. Zettlmeiβl et al., BIM, 82, 26–34, 1988) in which the AT III gene has been replaced by a polylinker) whose BamHI fragment had been replaced by an EcoRI linker. The clone (L) which contains the fusion gene was isolated (FIG. 11). The clone (L) was expanded and used for transfections in mammalian cells.

EXAMPLE 12

Figure 12:
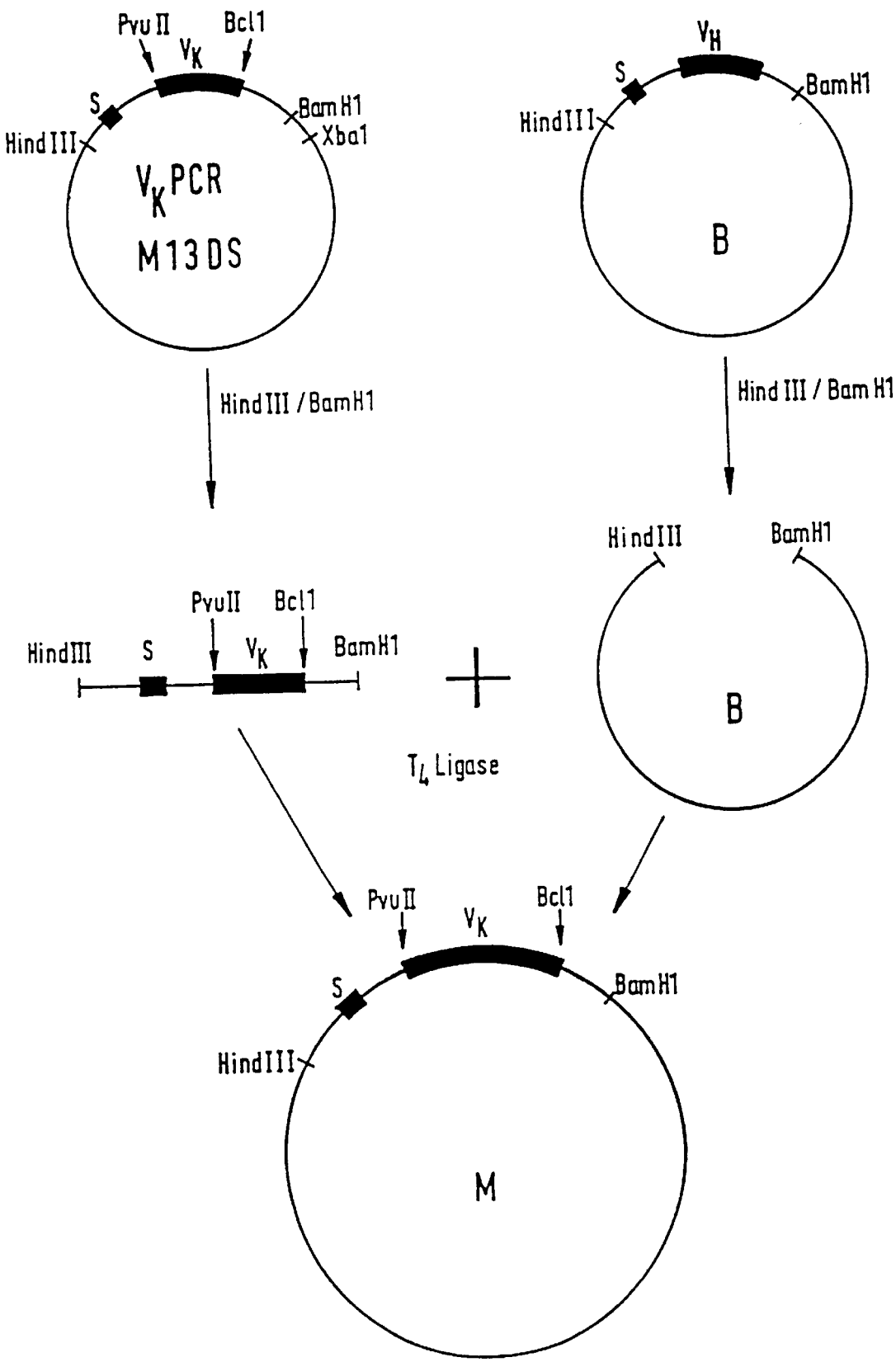

Construction of light chain gene: The phasmid clone (B) was cleaved with HindIII and BamHI, and the VH insert was replaced by the VK insert isolated from the vector VKPCR (R. Orlandi et al., 1989, loc. cit.). The phasmid clone (M)

which harbors a signal exon and a VK exon was isolated (FIG. 12). The phasmid clone was used to clone the amplified VK genes of MAbs I and II. The vector M with the VK1 gene was called M1 and the vector M with the VK2 gene was called M2.

EXAMPLE 13

Figure 13:
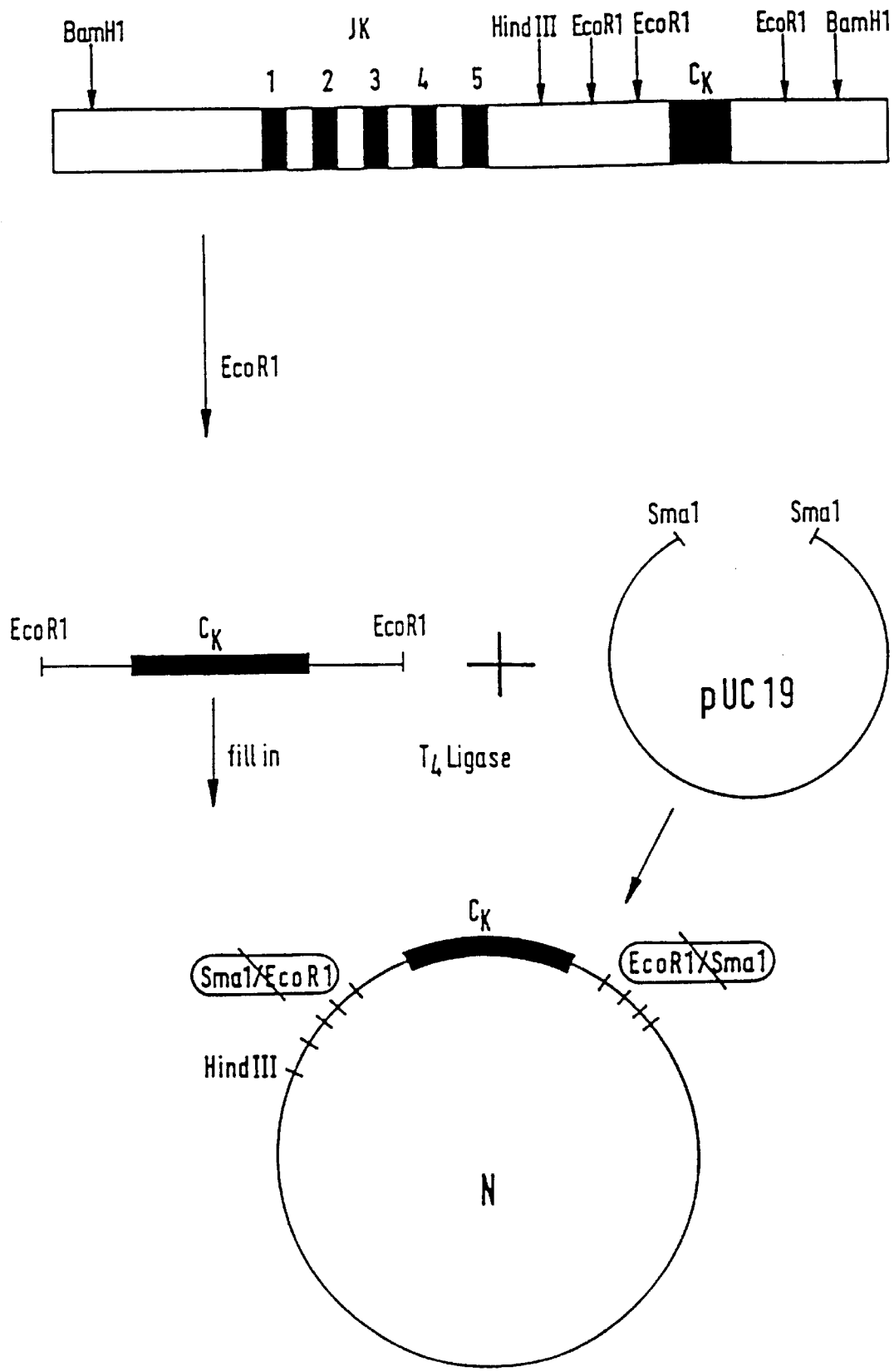

The human CK gene (Heiter et al., J. of Biol. Chem., 257: 1516–1522, 1982) was isolated as EcoRI fragment and cloned into the SmaI cleavage site of a pUC 19 plasmid. The clone (N) which contains the human CK gene was isolated (FIG. 13).

EXAMPLE 14

Figure 14:
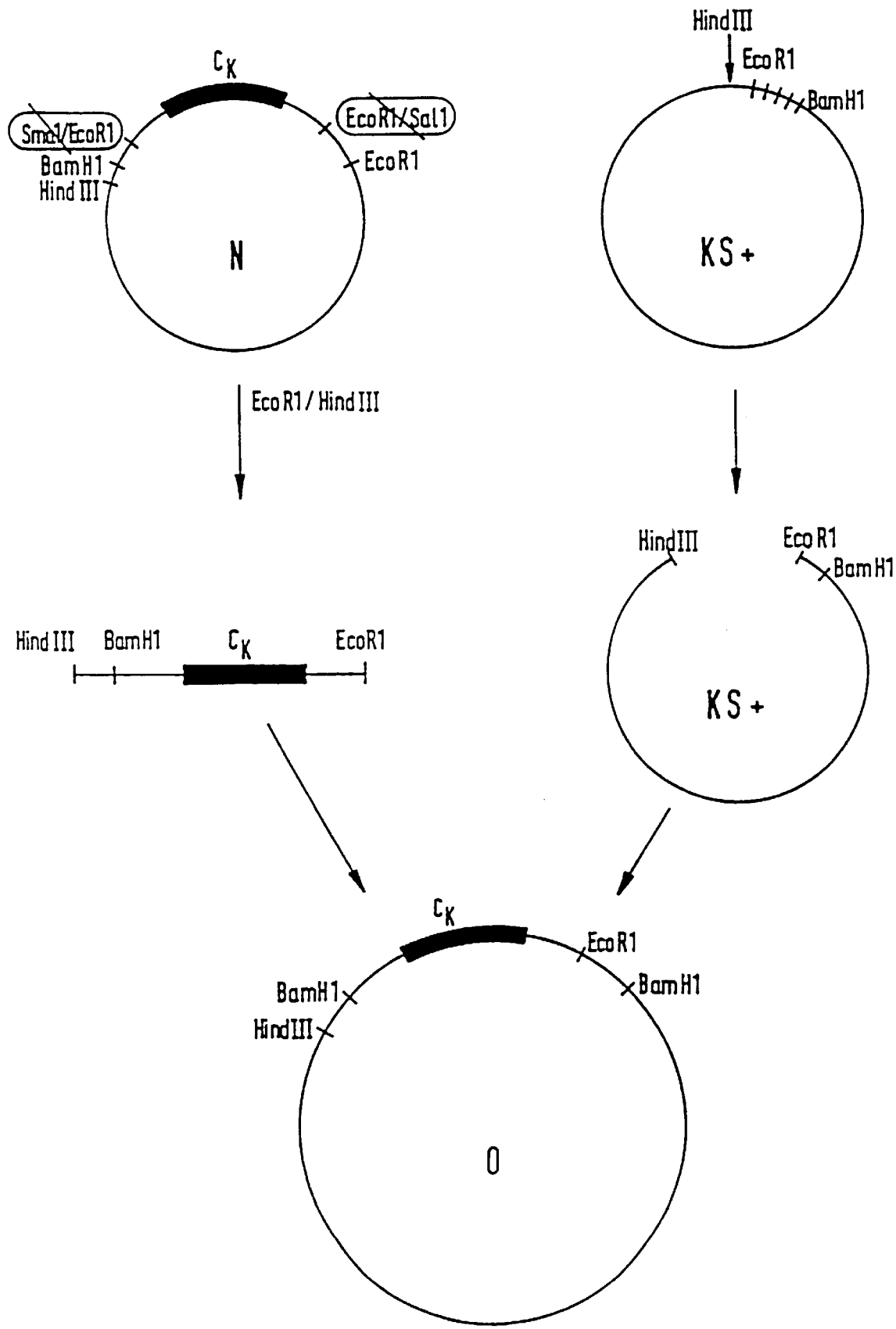

The clone (N) was cleaved with EcoRI and HindIII, and the CK insert was isolated and cloned into an EcoRI/HindIII-cleaved KS+ vector. The phasmid clone (O) which contains the CK insert was isolated (FIG. 14).

EXAMPLE 15

Figure 15:
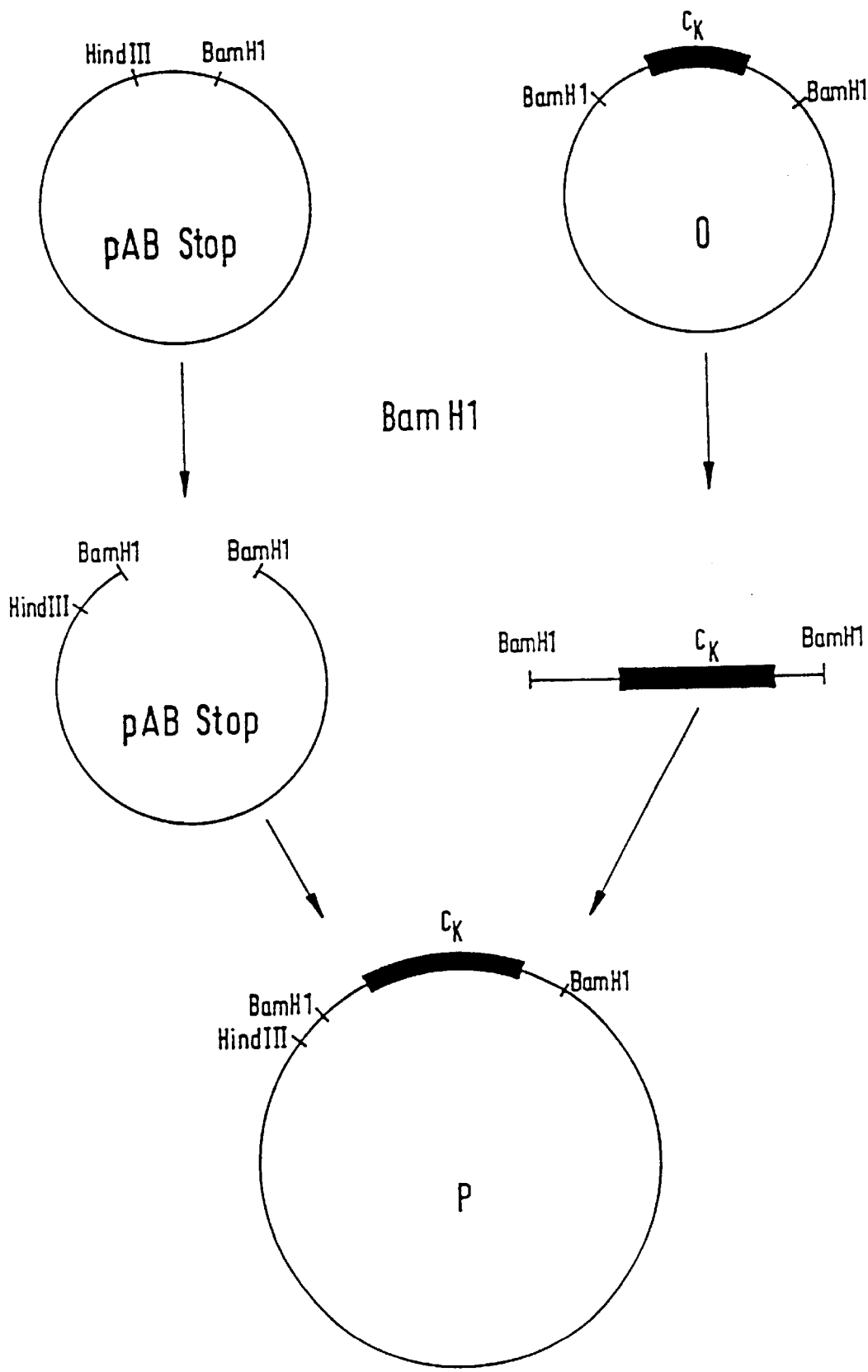

The clone (O) was cleaved with BamHI, and the CK insert was isolated and cloned into a BamHI-cleaved pAB Stop vector. The clone (P) which contains the CK insert in an orientation in which the 5' end of the CK gene is in the vicinity of the HindIII cleavage site of the pAB Stop vector was isolated (FIG. 15).

EXAMPLE 16

Figure 16:
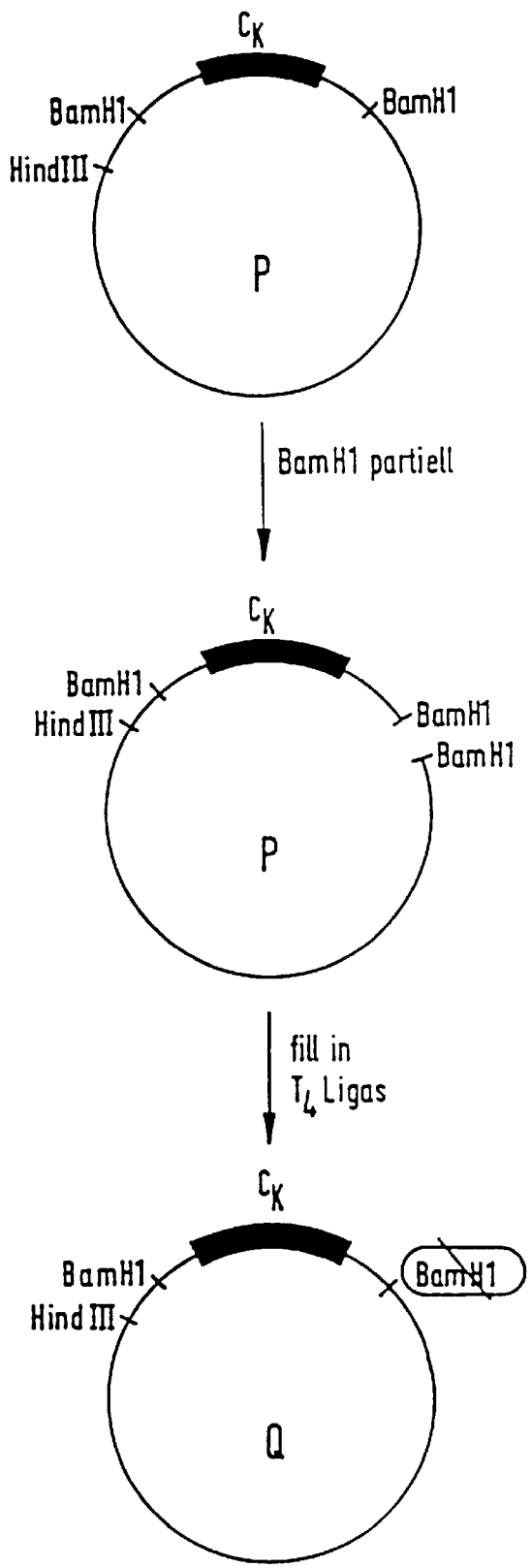

The clone (P) was partially cleaved with BamHI, and the cleavage sites were made blunt ended in with Klenow DNA polymerase and religated. The clone (Q) in which the BamHI cleavage site 3' of the CK gene is destroyed was identified (FIG. 16).

EXAMPLE 17

Figure 17:
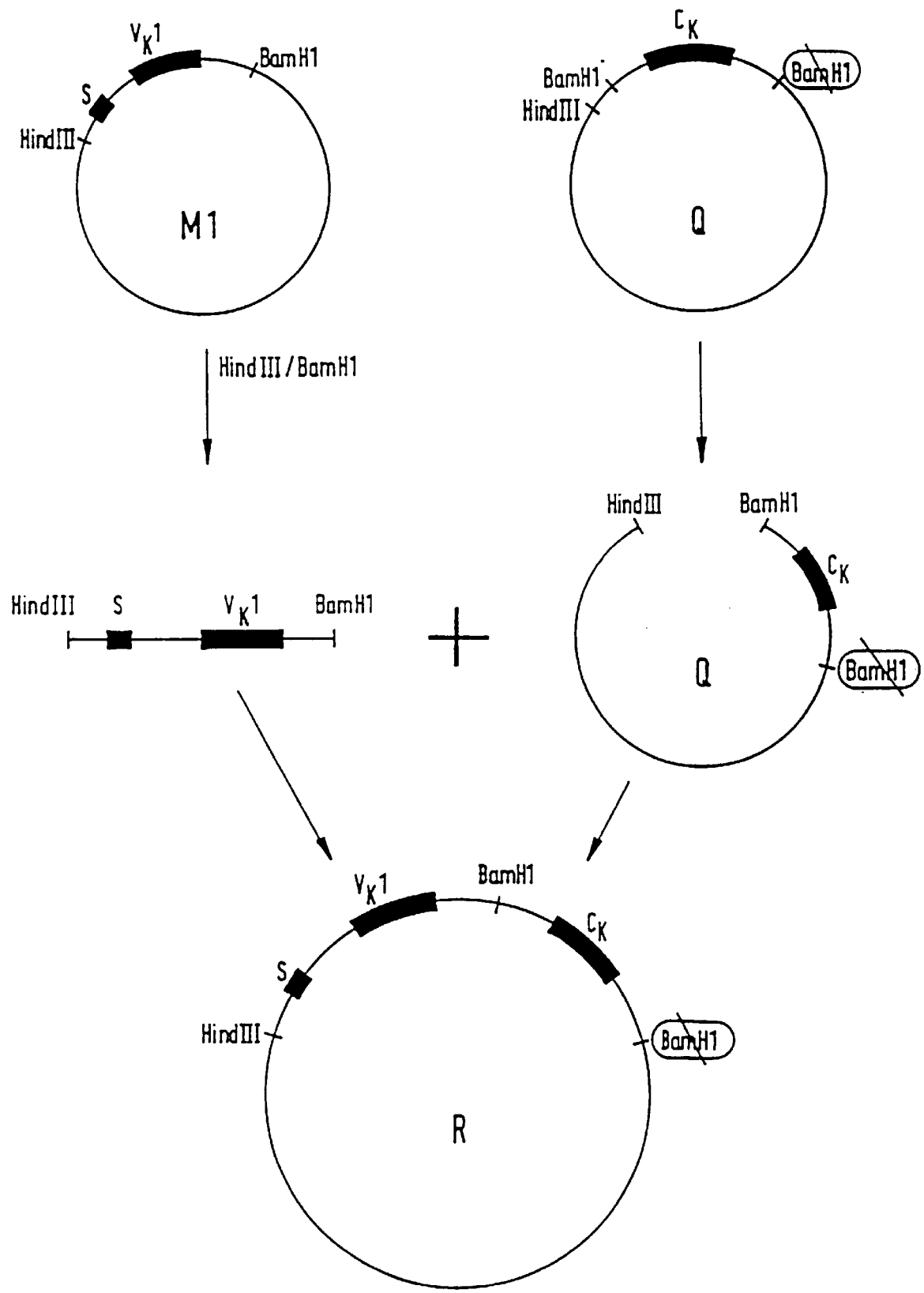

The phasmid clone (M1) with the VK1 gene was cleaved with HindIII and BamHI. The insert with the VK gene was isolated and ligated into the HindIII and BamHI cleavage site of the expression vector (Q). The clone (R) which contains an intact kappa light chain gene with the specificity of the antibody I was identified (FIG. 17).

EXAMPLE 18

Figure 18:
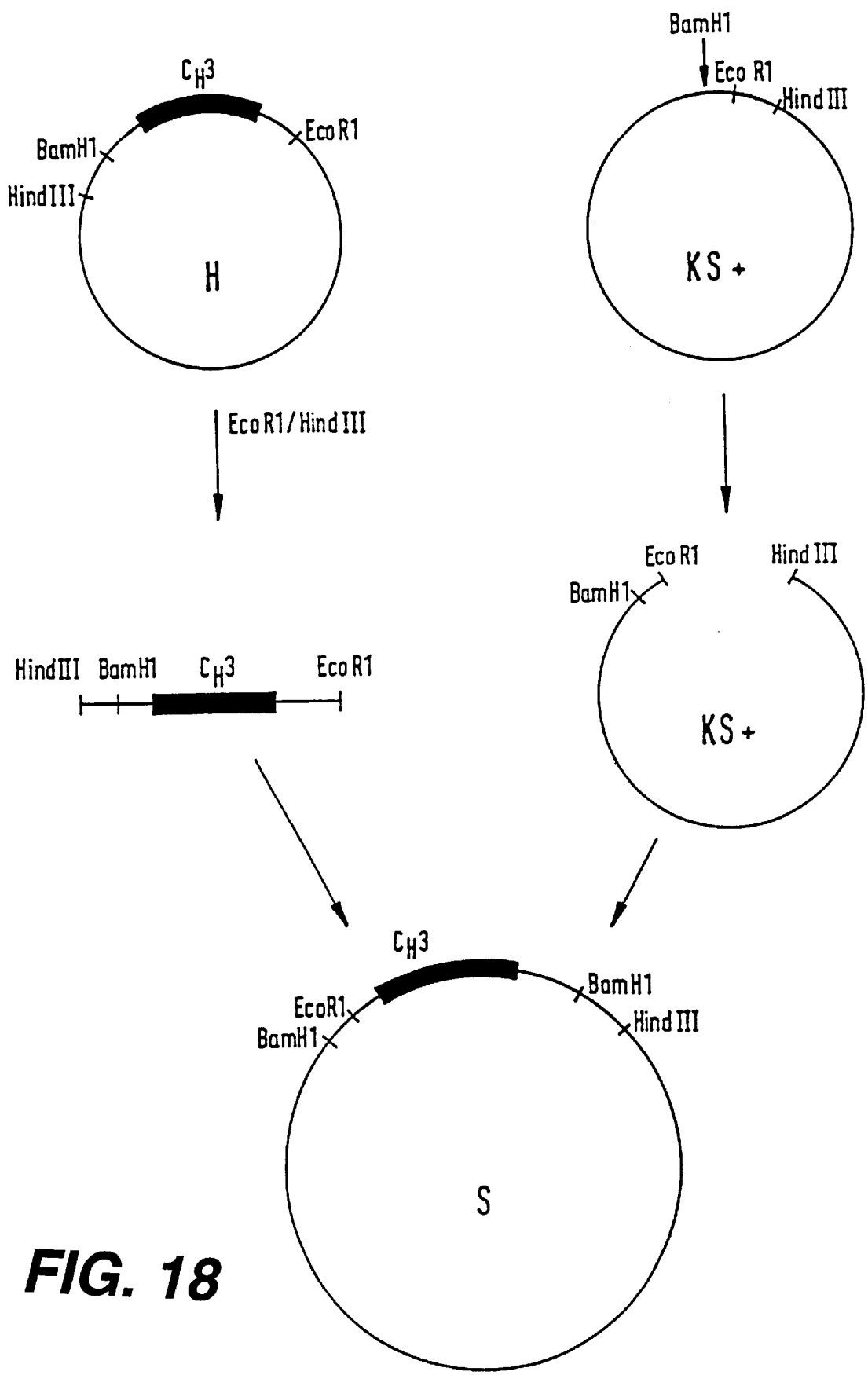

The plasmid clone (H) with the CH3 exon of the human IgG3 gene was cleaved with EcoRI and HindIII, and the CH3 insert was isolated and cloned into an EcoRI/HindIII-cleaved KS+ vector. The phasmid clone (S) which contains the CH3 insert was isolated (FIG. 18).

EXAMPLE 19

Figure 20:
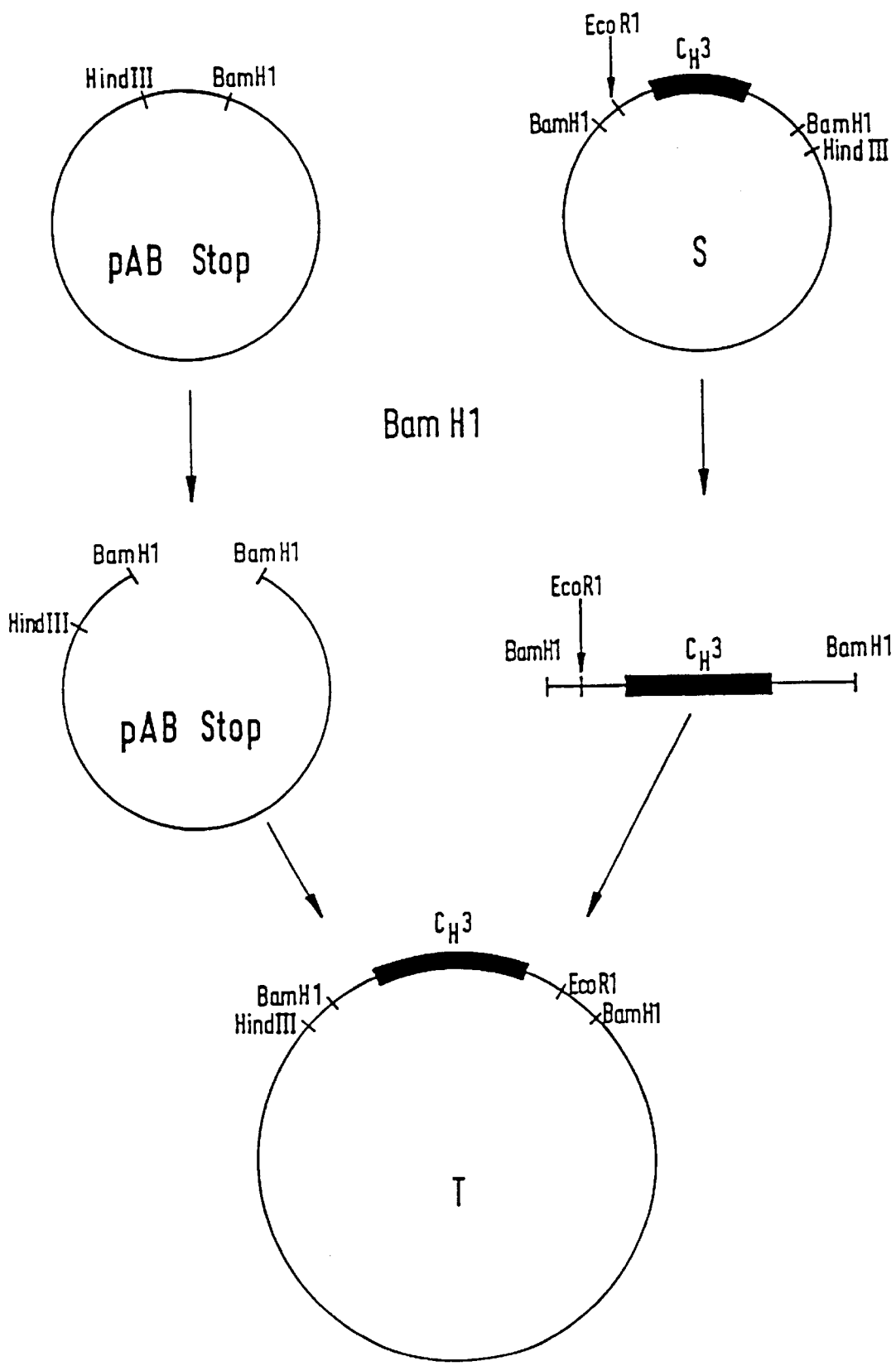

The clone (S) was cleaved with BamHI, and the CH3 insert was isolated and cloned into a BamHI-cleaved pAB Stop vector (FIG. 19). The clone (T) which contains the CH3 insert in an orientation in which the 5' end of the CH3 exon is in the vicinity of the HindIII cleavage site of the pAB Stop vector was isolated (FIG. 20).

EXAMPLE 20

Figure 21:
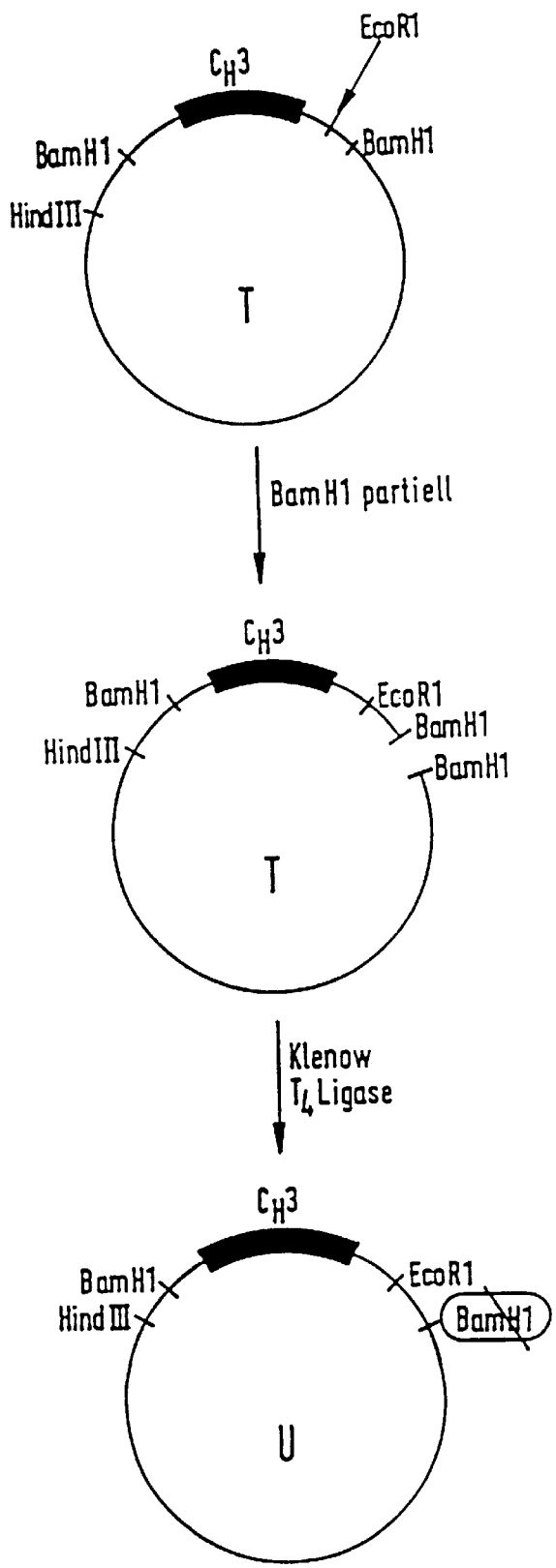

The clone (T) was partially cleaved with BamHI, and the cleavage site was made blunt ended in with Klenow DNA polymerase and religated. The clone (U) in which the BamHI cleavage site 3' of the CH3 gene is destroyed was identified (FIG. 21).

EXAMPLE 21

Figure 22:
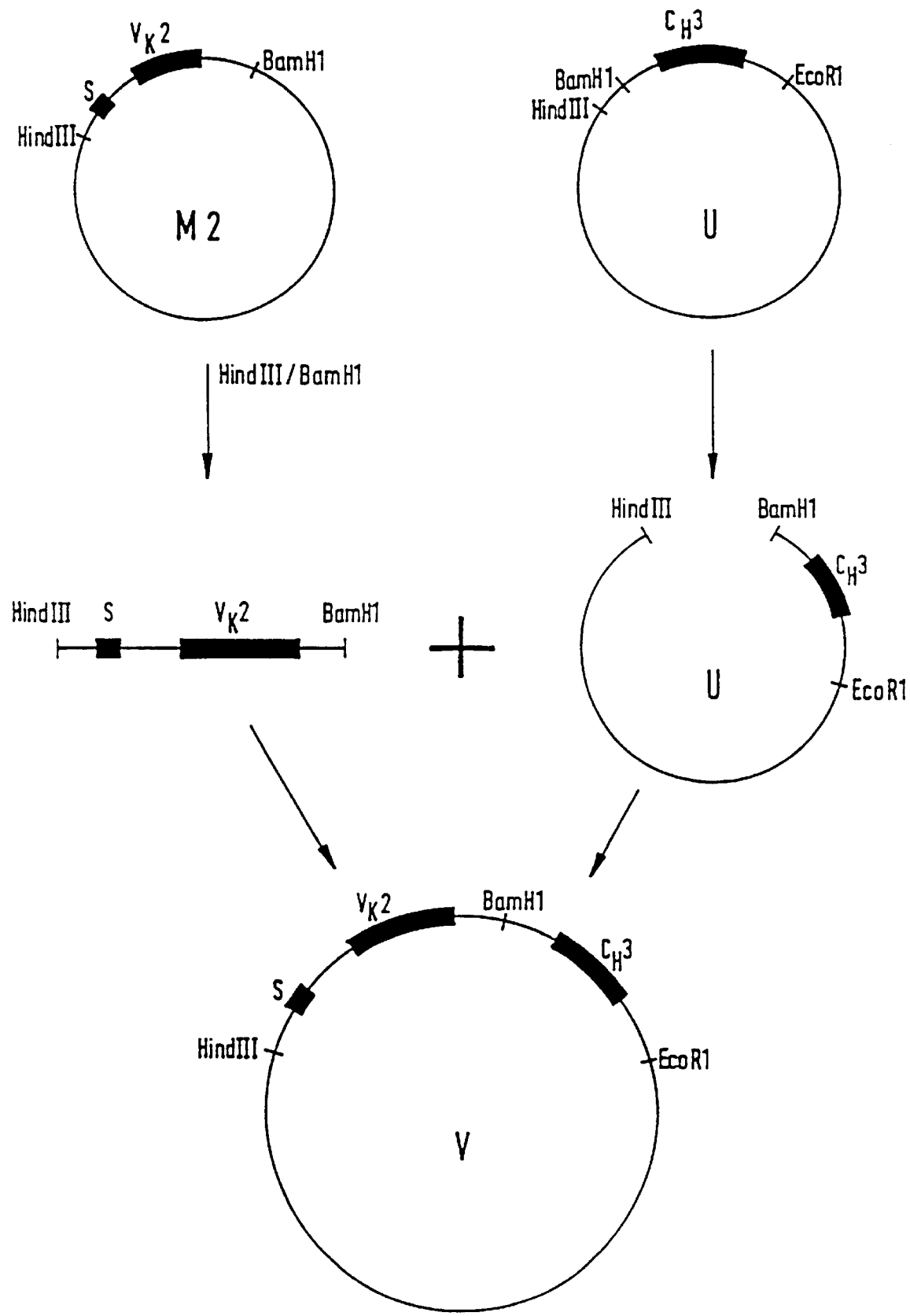

The phasmid clone (M2) with the VK2 gene was cleaved with HindIII and BamHI. The insert with the VK gene was isolated and ligated into the HindIII and BamHI cleavage sites of the expression vector (U). The clone (V) which contains an intact light chain gene with the specificity of the antibody II and a CH3 exon as constant region was identified (FIG. 22).

Figure 23:
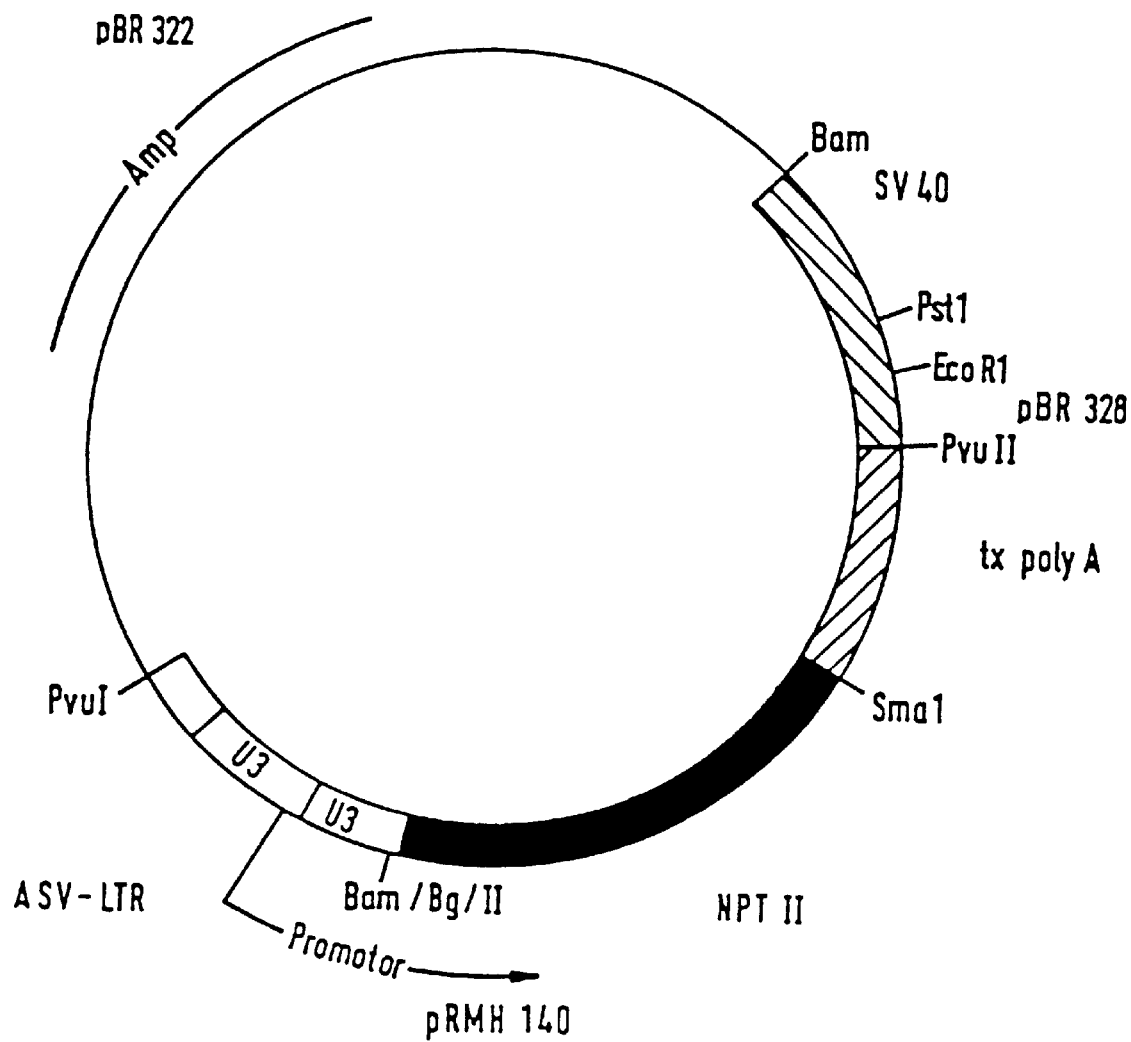
Figure 24:
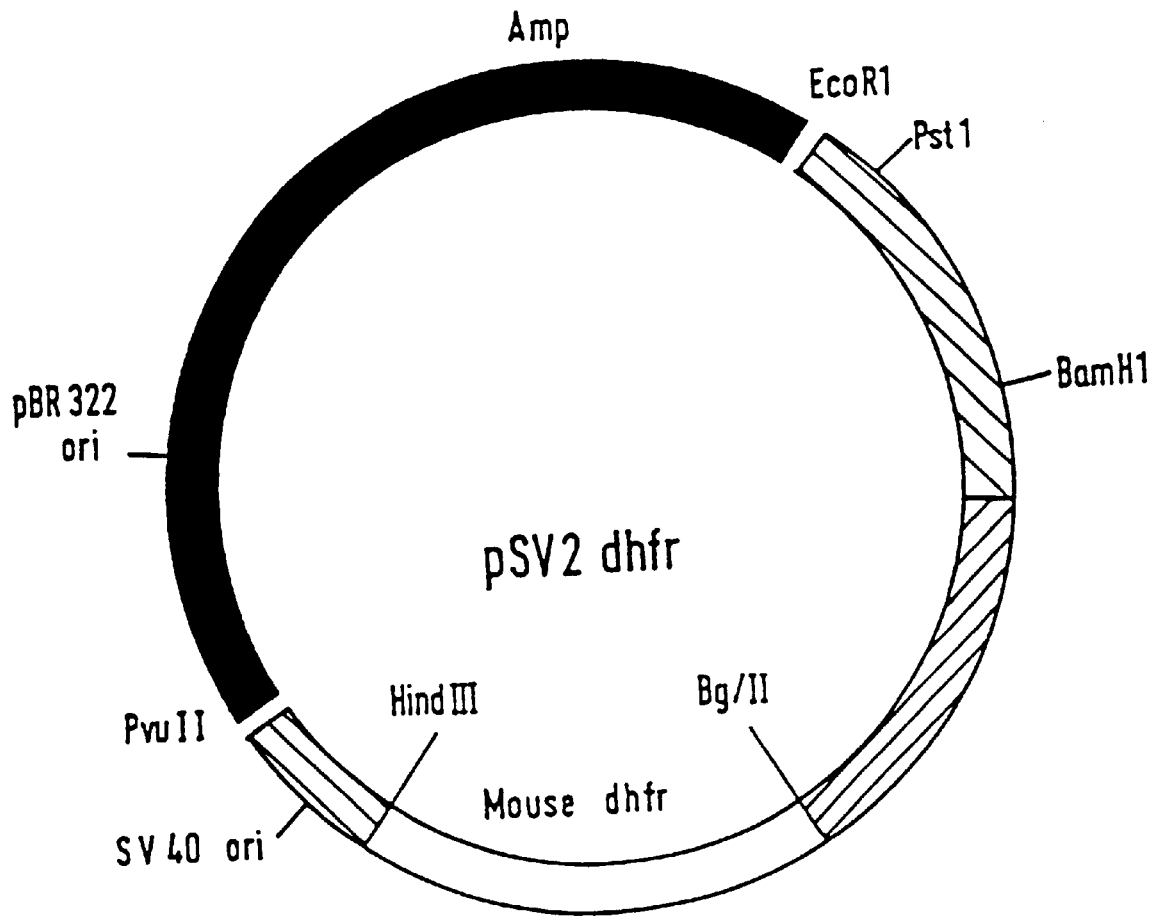

The expression plasmids L, R and V were cotransfected (30) together with suitable phasmids harboring selection markers, such as, for example, pRMH140 (FIG. 23) (R. M. Hudziak et al., 1982, loc. cit.) or pSV2dhfr (FIG. 24) (F. Lee et al., 1981, loc. cit.) into mammalian cells, transfectoma clones were selected by selection pressure, and those transfectoma clones which secrete bivalent tetraspecific receptor molecules were identified by assaying the supernatants with suitable assays.

We claim:

1. A bispecific, tetravalent antibody of FIG. 25 or FIG. 26 wherein H L represents an amino acid sequence comprising one or more hinge regions (H) and a linker peptide (L), thick lines represent peptide bonds, thin lines represent disulfide bridges connecting the two polypeptide chains of said antibody, and wherein the VL1 and VH1 domains of FIGS. 25 and 26 correspond to such domains of a first antibody and are paired naturally, the VL2 and VH2 domains of FIGS. 25 and 26 correspond to such domains of a second, different antibody and are paired naturally, and wherein the CH1 domains are bound to the VH2 domains by 1 to 10 hinge regions H and a suitable linker peptide L.

2. An antibody as claimed in claim 1, wherein the specificity of either the first antibody or the second antibody is directed against animal or human tumor-associated antigen.

3. An antibody as claimed in claim 1, wherein the specificity of either the first antibody or the second antibody has catalytic or enzymatic activity.

4. An antibody as claimed in claim 1, wherein the specificity of either the fast antibody or the second antibody is directed against animal or human tumor-associated antigen and the other antibody has catalytic or enzymatic activity.

5. An antibody as claimed in claim 1, wherein the specificity of either the fist antibody or the second antibody is directed against animal or human tumor-associated antigen and the other antibody specificity is directed against a complexon.

6. An antibody as claimed in claim 1, wherein the variable domains from the first antibody or the second antibody (II) are selected from the group comprising the variable domains of FIGS. 27–34.

7. A pharmaceutical composition comprising an effective amount of an antibody as claimed in claim 1 together with a pharmaceutically acceptable carrier or excipient.

Figure 25:
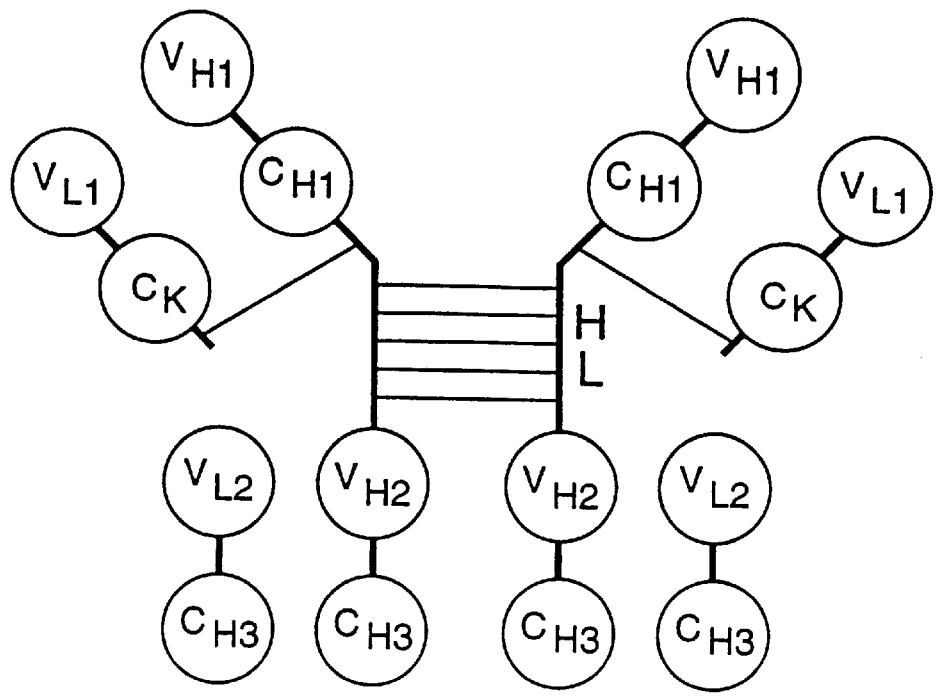
Figure 26:
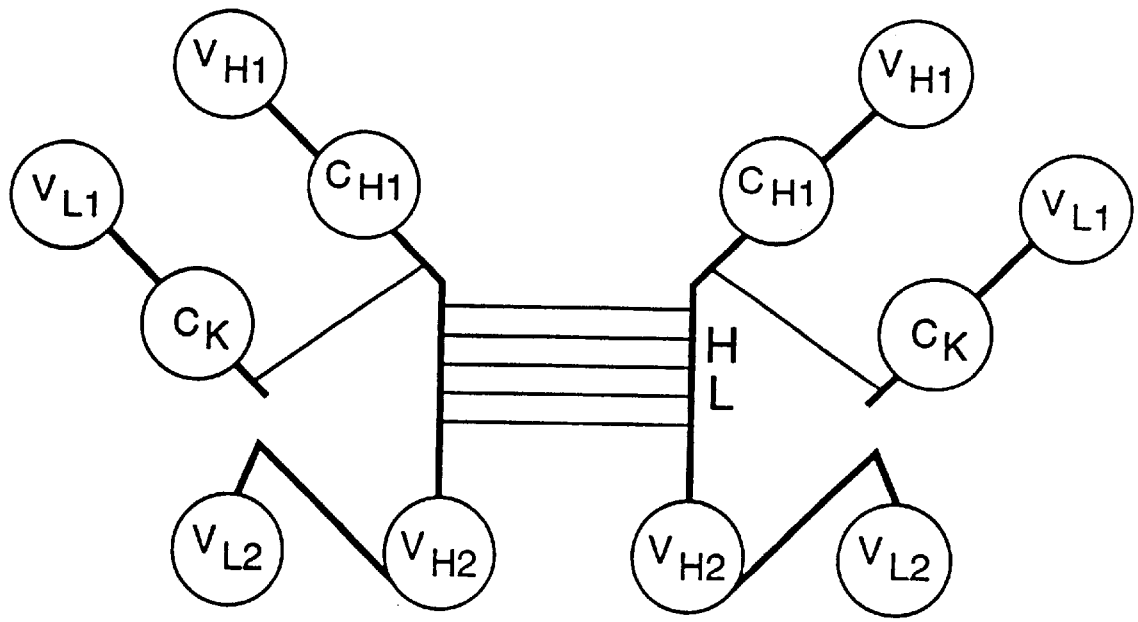

8. A process for the preparation of an antibody as claimed in claim 1, which comprises providing DNA fragments coding for each polypetide chain comprising either VH1, CH1, VH2, CH3, or VL1, CK, or VL2, CH3, or VH1, CH1, VH2, VL2, or VL1, CK, as shown in FIGS. 25 or 26, connecting the appropriate domains by DNA coding for linkers, where appropriate, and expressing the appropriate combination of polypetide chains in a suitable expression system.

9. A bispecific, tetravalent antibody of FIG. 25 wherein H L represents an amino acid sequence comprising one or more hinge regions (H) and a linker peptide (L), thick lines represent peptide bonds, thin lines represent disulfide bridges connecting the two polypeptide chains of said antibody, in which the CH3 domains are replaced by human CH1 domains.

* * * * *

UNITED STATES PATENT AND TRADEMARK OFFICE
CERTIFICATE OF CORRECTION

PATENT NO. : 5,959,083
DATED : September 28, 1999
INVENTOR(S) : Klaus BOSSLET, et al It is certified that error appears in the above-identified patent and that said Letters Patent is hereby corrected as shown below:

Claim 4, Column 23, line 43, "fast" should read --first--.

Claim 5, Column 23, line 47, "fist" should read --first--.

Signed and Sealed this

Fifteenth Day of August, 2000

Attest:

Q. TODD DICKINSON

Attesting Officer

Director of Patents and Trademarks